United States Patent [19]

Genain

[11] Patent Number: 4,761,420

[45] Date of Patent: Aug. 2, 1988

[54] ANTIHYPERTENSIVE DIHYDROPYRIDINE DERIVATIVES

[75] Inventor: Gilles Genain, Issy-les-Moulineaux, France

[73] Assignee: Laboratoires Syntex S.A., Puteaux Cedex, France

[21] Appl. No.: 874,264

[22] Filed: Jun. 13, 1986

[51] Int. Cl.$^4$ .................. A61K 31/455; C07D 211/90; C07D 405/12

[52] U.S. Cl. ................... 514/336; 514/356; 546/268; 546/283; 546/321

[58] Field of Search ................ 546/321, 283, 268; 514/336, 356

[56] References Cited

U.S. PATENT DOCUMENTS

| | | | |
|---|---|---|---|
| 4,044,141 | 8/1977 | Bossert et al. | 546/321 |
| 4,595,690 | 6/1986 | Clark et al. | 514/356 |

FOREIGN PATENT DOCUMENTS

| | | |
|---|---|---|
| 145434 | 6/1985 | European Pat. Off. |
| 161877 | 11/1985 | European Pat. Off. |
| WO84/02132 | 6/1984 | PCT Int'l Appl. |

*Primary Examiner*—Richard A. Schwartz
*Assistant Examiner*—Dale A. Bjorkman
*Attorney, Agent, or Firm*—Grant D. Green; Tom M. Moran; Brian Lewis

[57] ABSTRACT

Compound of formula 1 are calcium entry antagonists useful for treating hypertension, congestive heart failure, angina, and vasospastic disorders:

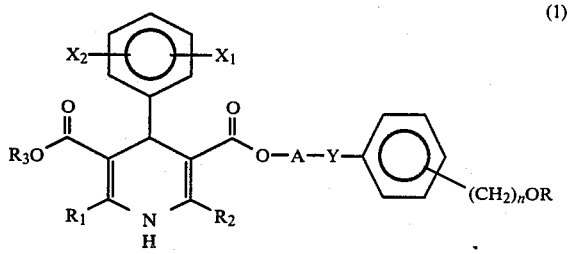

(1)

wherein
n is an integer from 1 to 4;
$R_1$ and $R_2$ are lower alkyl;
$R_3$ is lower alkyl or alkoxyalkyl;
A is alkylene of two to eight carbon atoms;
$X_1$ and $X_2$ are each independently —$NO_2$, —$CF_3$, $CH_3O$—, —CN, —H, lower alkyl or halo;
Y is —O—, —S—, —S(O)—, or —$S(O)_2$—; and
R is H, lower alkyl, cycloalkyl, alkoxyalkyl, cycloalkyloxy-alkyl, alkoxycycloalkyl, acyl, or saturated or unsaturated 5- or 6-membered heterocyclyl optionally substituted with lower alkyl or alkoxy, wherein the heteroatom is one oxygen atom.

35 Claims, No Drawings

ANTIHYPERTENSIVE DIHYDROPYRIDINE DERIVATIVES

BACKGROUND OF THE INVENTION

1. Field of the Invention

This invention relates to 4-phenyl-1,4-dihydropyridine derivatives which are useful in the treatment of cardiovascular diseases such as hypertension, congestive heart failure, angina, migraine, and vasospastic disorders. The invention also relates to a pharmaceutically acceptable composition containing an effective amount of at least one of the compounds in combination with a suitable excipient, the composition being useful for the treatment of cardiovascular diseases such as hypertension, congestive heart failure, angina, migraine, and vasospastic disorders in mammals. The invention also relates to a process for making the compounds of the invention, and the use of compounds of the invention in pharmaceutical compositions useful for the treatment of cardiovascular diseases such as hypertension, congestive heart failure, angina, migraine, and vasospastic disorders in mammals.

The invention also relates to intermediates and processes for preparing optically active compounds of the invention.

2. Related Disclosures

Certain 4-aryl-1,4-dihydropyridine derivatives are known calcium entry antagonists. See, for example, U.S. Pat. Nos. 3,485,847 and 4,044,141. Novel 4-phenyl-1,4-dihydropyridine derivatives with high efficacy and long duration of action have now been prepared.

It is known that, for most cardiovascular-active dihydropyridine derivatives, the isomer which has an (S) configuration at C4 in the dihydropyridine ring is more active than the (R) isomer. Compounds with the (S) configuration may be prepared from (−)-2,6-dimethyl-3-carbomethoxy-4-(3-nitrophenyl)-5-carboxy-1,4-dihydropyridine. This (S) isomer may be prepared following the method of T. Shibanuma, et al., Chem. Pharm. Bull., 28, 2809-2812 (1980). Now, a more efficient, effective, and less expensive method for preparing optically active mono-esterified dihydropyridine derivatives has been discovered.

SUMMARY OF THE INVENTION

The first aspect of this invention is the group of compounds represented by the formula

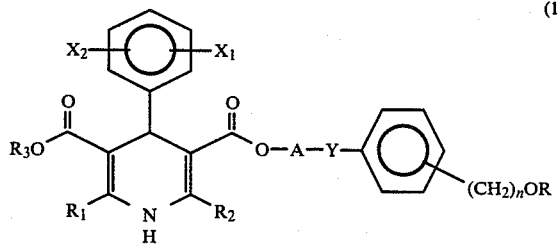

(1)

wherein
n is n integer from 1 to 4;
$R_1$ and $R_2$ are lower alkyl;
$R_3$ is lower alkyl or alkoxyalkyl;
A is alkylene of two to eight carbon atoms;
$X_1$ and $X_2$ are each independently $-NO_2$, $-CF_3$, $CH_3O-$, $-CN$, $-H$, lower alkyl or halo;

Y is $-O-$, $-S-$, $-S(O)-$, or $-S(O)_2-$; and
R is H, lower alkyl, cycloalkyl, alkoxyalkyl, cycloalkyloxy-alkyl, alkoxycycloalkyl, acyl, or saturated or unsaturated 5- or 6-membered heterocyclyl optionally substituted with lower alkyl or alkoxy, wherein the heteroatom is one oxygen atom.

Another aspect of the invention is a composition useful in the treatment of a cardiovascular disease treatable with a calcium-entry antagonist, which method comprises administering to a subject in need thereof an effective amount of a compound of formula 1 and a pharmaceutically suitable excipient.

Still another aspect of the invention is a method for treating cardiovascular diseases such as hypertension, congestive heart failure, angina, migraine, and vasospastic disorders in mammals which comprises administering an effective amount of at least one compound chosen from those represented by formula 1 above.

Another aspect of the invention is the intermediate of formula 18

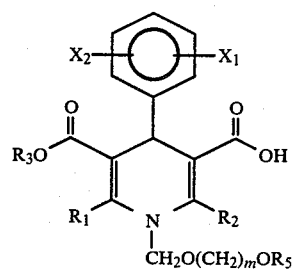

(18)

and the basic addition salts thereof, wherein
m is 1, 2, or 3;
$R_1$ and $R_2$ are lower alkyl;
$R_3$ is lower alkyl or alkoxyalkyl;
$R_5$ is lower alkyl; and
$X_1$ and $X_2$ are each independently $-NO_2$, $-CF_3$, $CH_3O-$, $-CH$, $-H$, lower alkyl or halo.

Still another aspect of the invention is a process for preparing optically active compounds of formula 19

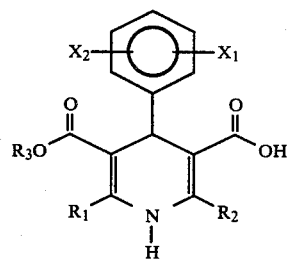

(19)

and the basic addition salts thereof, wherein
$R_1$ and $R_2$ are lower alkyl;
$R_3$ is lower alkyl or alkoxyalkyl; and
$X_1$ and $X_2$ are each independently $-NO_2$, $-CF_3$, $CH_3O-$, $-CN$, $-H$, lower alkyl or halo.

DETAILED DESCRIPTION AND PREFERRED EMBODIMENTS

The broadest aspect of the present invention is the group of compounds represented by the formula

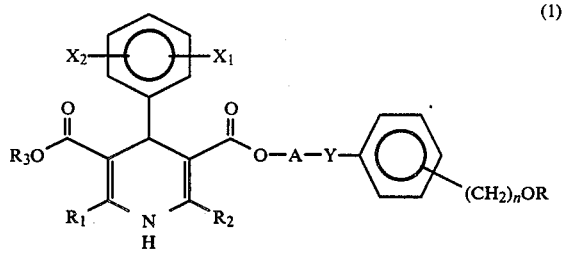

(1)

wherein
n is an integer from 1 to 4;
$R_1$ and $R_2$ are lower alkyl;
$R_3$ is lower alkyl or alkoxyalkyl;
A is alkylene of two to eight carbon atoms;
$X_1$ and $X_2$ are each independently —$NO_2$, —$CF_3$, $CH_3O$—, —CH, —H, lower alkyl or halo;
Y is —O—, —S—, —S(O)—, or —S(O)$_2$—; and
R is H, lower alkyl, cycloalkyl, alkoxyalkyl, cycloalkyloxy-alkyl, alkoxycycloalkyl, acyl, or saturated or unsaturated 5- or 6-membered heterocyclyl optionally substituted with lower alkyl or alkoxy, wherein the heteroatom is one oxygen atom. A preferred subgenus is the compound wherein $R_1$ and $R_2$ are each methyl, particularly where Y is —O—, and especially where the configuration at C4 is (S). A preferred class of the invention is the compound where n is 2, especially where A is propylene. A preferred subclass is the compound where $X_1$ is 3—$NO_2$ and $X_2$ is —H. A preferred embodiment of the invention is the compound where R is tetrahydropyran-2-yl. Another preferred compound is the compound where R is —H. Another preferred compound is the compound where R is methyl or propyl. Another preferred compound is the compound where R is propoxy-methyl or cyclohexyloxy-methyl.

Another preferred subclass is the compound where $X_1$ is 2—Cl and $X_2$ is 3—Cl. A preferred embodiment is the compound where R is tetrahydropyran-2-yl. Another preferred embodiment is the compound where R is —H.

Another preferred class of the invention is the compound where n is 2 and A is ethylene. A preferred subclass is the compound where $X_1$ is 3—$NO_2$ and $X_2$ is —H. A preferred embodiment is the compound where R is tetrahydropyran-2-yl. Another preferred embodiment is the compound where R is —H, methyl, or propyl. Another preferred embodiment is the compound where R is propoxy-methyl or cyclohexyloxy-methyl.

Another preferred class of the invention is the compound where n is 3, especially where A is ethylene or propylene. A preferred subclass is the compound where $X_1$ is 3—$NO_2$ and $X_2$ is —H. A preferred embodiment is the compound where R is tetrahydropyran-2-yl. Another preferred embodiment is the compound where R is —H, methyl, or propyl. Another preferred embodiment is the compound where R is propoxy-methyl or cyclohexyloxymethyl.

Another aspect of the invention is a pharmaceutical composition comprising a pharmaceutically acceptable excipient and an effective amount of a compound of formula 1. A preferred subgenus is the composition wherein the compound of formula 1 is
(S,RS)-2,6-dimethyl-3-carbomethoxy-4-(b 3-nitrophenyl)-5-[3-(4-[2-(tetrahydropyran-2-yloxy)ethyl]-phenoxy)propoxycarbonyl]-1,4-dihydropyridine, (S)-2,6-dimethyl-3-carbomethoxy-4-(3-nitrophenyl)-5-(3-[4-(2-hydroxyethyl)phenoxy]propoxycarbonyl)-1,4-dihydropydridine, (S)-2,6-dimethyl-3-carbomethoxy-4-(3-nitrophenyl)-5-(3-[4-(2-methoxyethyl)phenoxy]propoxycarbonyl)-1,4-dihydropyridine, (S)-2,6-dimethyl-3-carbomethoxy-4-(3-nitrophenyl)-5-(3-[4-(2-propoxyethyl)phenoxy]propoxycarbonyl)-1,4-dihydropyridine, (S)-2,6-dimethyl-3-carbomethoxy-4-(3-nitrophenyl)-5-[3-(4-[2-(propoxymethoxy)ethyl]phenoxy)propoxycarbonyl]-1,4-dihydropyridine, or (S)-2,6-dimethyl-3-carbomethoxy-4-(3-nitrophenyl)-5-[3-(4-[2-(cyclohexyloxymethoxy)ethyl]phenoxy)-propoxycarbonyl]-1,4-dihydropyridine.

Another aspect of the invention is a method for treating cardiovascular diseases treatable with calcium-entry antagonists, which method comprises administering to a subject in need thereof an effective amount of a compound of formula 1.

Another aspect of the invention is a compound of formula 18

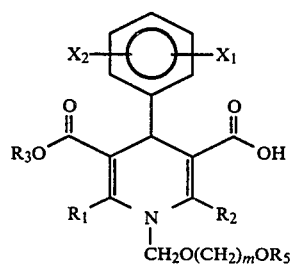

(18)

and the basic addition salts thereof, wherein
m is 1, 2, or 3;
$R_1$ and $R_2$ are lower alkyl;
$R_3$ is lower alkyl or alkoxyalkyl;
$R_5$ is lower alkyl; and
$X_1$ and $X_2$ are each independently —$NO_2$, —$CF_3$, $CH_3O$—, —CN, —H, lower alkyl or halo. A preferred class is the compound wherein $R_1$, $R_2$ and $R_3$ are each methyl, $X_1$ is 3—$NO_2$, and $X_2$ is —H, particularly where m is 2 and $R_5$ is methyl. A preferred subclass is the compound which is ($\pm$)-1-(2-methoxyethoxymethyl)-2,6-dimethyl-3-carbomethoxy-4-(3-nitrophenyl)-5-carboxy-1,4-dihydropyridine or a basic addition salt thereof. A preferred embodiment is the compound (+)-1-(2-methoxyethoxymethyl)-2,6-dimethyl-3-carbomethoxy-4-(3-nitrophenyl)-5-carboxy-1,4-dihydropyridine or a basic addition salt thereof. Another preferred embodiment is the cinchonidine salt of (+)-1-(2-methoxyethoxymethyl)-2,6-dimethyl-3-carbomethoxy-4-(3-nitrophenyl)-5-carboxy-1,4-dihydropyridine.

Another aspect of the invention is a process, which process comprises:

contacting a suitable optically active base, or a mixture of a suitable optically active base with an optically inactive base, with a compound of formula 18

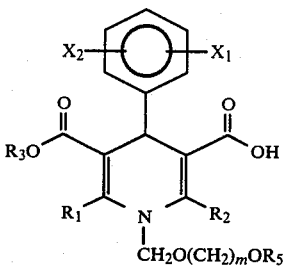

(18)

wherein
m is 1, 2, or 3;
$R_1$ and $R_2$ are lower alkyl;
$R_3$ is lower alkyl or alkoxyalkyl;
$R_5$ is lower alkyl; and
$X_1$ and $X_2$ are each independently —$NO_2$, —$CF_3$, $CH_2O$—, —CN, —H, lower alkyl or halo;
in a ratio of optically active base to compound of formula 18 between about 0.8:1 to 1.4:1, or a ratio of optically active base to optically inactive base to compound of formula 18 of about 1:1:2, to a suitable lower alkanol solvent at a temperature within about 10° C. of the reflux temperature of said lower alkanol solvent; and allowing the resulting insoluble optically active compound of formula 18.optically active base salt to crystallize. A preferred subgenus is the process wherein said suitable optically active base is cinchonidine, particularly where said suitable lower alkanol solvent is ethanol. A preferred class is the process which further comprises cleaving said insoluble compound of formula 18.optically active base salt with a soft acid or a mineral acid in a concentration between about 0.1N and 0.65N in a suitable water non-miscible solvent to produce an optically active compound of formula 18, particularly where said mineral acid is 0.6N hydrochloric acid. A preferred subclass of the invention is the process which further comprises hydrolyzing said optically active compound of formula 18 with a mineral acid in a concentration between about 0.8N and about 2.4N, in a suitable water-miscible solvent at a temperature between the freezing point of the acid/solvent mixture and about 15° C. to produce an optically active compound of formula 19;

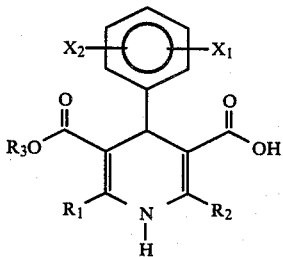

(19)

and the basic addition salts thereof, wherein
$R_1$ and $R_2$ are lower alkyl;
$R_3$ is lower alkyl or alkoxyalkyl; and
$X_1$ and $X_2$ are each independently —$NO_2$, —$CF_3$, $CH_3O$—, —CN, —H, lower alkyl or halo, particularly the process which further comprises precipitating said optically active compound of formula 19 by adding water to said water-miscible solvent, especially where said suitable water-miscible solvent is acetone and said mineral acid is 1N hydrochloric acid. A presently preferred embodiment is the process wherein $R_1$, $R_2$, and $R_3$ are each methyl, $X_1$ is 3-nitro, and $X_2$ is —H.

Another preferred embodiment of the invention is a process for preparing (−)-2,6-dimethyl-3-carbomethoxy-4-(3-nitrophenyl)-5-carboxy-1,4-dihydropyridine and the basic addition salts thereof, which process comprises:

contacting cinchonidine and 1-(2-methoxyethoxymethyl)-2,6-dimethyl-3-carbomethoxy-4-(3-nitrophenyl)-5-carboxy-1,4-dihydropyridine in a ratio of about 1:1 with ethanol at a temperature between about 70° and 85° C.;

allowing the resulting insoluble (−)-1-(2-methoxyethoxymethyl)-2,6-dimethyl-3-carbomethoxy-4-(3-nitrophenyl)-5-carboxy-1,4-dihydropyridine.cinchonidine salt to crystallize;

cleaving said insoluble salt with HCl at a concentration of about 0.6N in a water non-miscible solvent, preferably ethyl acetate or ether, to produce (+)-1-(2-methoxyethoxymethyl)-2,6-dimethyl-3-carbomethoxy-4-(3-nitrophenyl)-5-carboxy-1,4-dihydropyridine; and hydrolyzing said (+)-1-(2-methoxyethoxymethyl)-2,6-dimethyl-3-carbomethoxy-4-(3-nitrophenyl)-5-carboxy-1,4-dihydropyridine with 1N hydrochloric acid in acetone or tetrahydrofuran to produce (−)-2,6-dimethyl-3-carbomethoxy-4-(3-nitrophenyl)-5-carboxy-1,4-dihydropyridine.

DEFINITIONS

As used in the specification and appended claims, unless specified to the contrary, the following terms have the meaning indicated:

The term "lower alkyl" refers to a straight or branched chain monovalent radical consisting solely of carbon and hydrogen, containing no unsaturation and having from one to four carbon atoms. Examples of lower alkyl groups are methyl, ethyl, n-propyl, i-propyl, n-butyl, i-butyl, s-butyl and t-butyl.

The term "alkylene" refers to a straight chain divalent radical of the form —$(CH_2)_x$—, where x is an integer from 2 to 8. Examples of alkylene radicals include ethylene, propylene, butylene, pentalene, hexylene, heptalene, and octalene.

The term "cycloalkyl" refers to a cyclic hydrocarbon radical containing no unsaturation and having from three to eight carbon atoms. Examples of cycloalkyl groups are cyclopropyl, cyclohexyl, cyclohexylmethyl, 3-methylcyclopentyl and the like.

The term "alkoxy" refers to a radical of the form $R_aO$—, where $R_a$ is lower alkyl as defined above.

The term "alkoxyalkyl" refers to radicals of the form —$R_b$—O—$R_a$, where $R_b$ is alkylene of one to six carbon atoms, and $R_a$ is lower alkyl as defined above. Examples of alkoxyalkyl groups are methoxymethyl, methoxyethyl, 2-(2-propoxy)ethyl, t-butoxymethyl, and the like.

The term "cycloalkyloxy-alkyl" refers to radicals of the form —$R_b$—O—$R_c$, where $R_c$ is cycloalkyl and $R_b$ is alkylene of one to six carbon atoms, as defined above. Examples of cycloalkyloxy-alkyl groups are cyclohexyloxy-methyl, cyclohexyloxy-ethyl, cyclopentyloxymethyl, cyclohexyloxy-butyl, cyclopropyloxy-methyl, and cyclooctyloxy-butyl.

The term "alkoxy-cycloalkyl" refers to radicals of the form —$R_c$—O—$R_a$, where $R_c$ is cycloalkylene (a divalent cycloalkyl radical of three to eight carbon atoms) and $R_a$ is lower alkyl, as defined above. Examples of alkoxy-cycloalkyl groups are 4-methoxycyclohexyl, 3-ethoxy-cyclopentyl, methoxy-cyclopropyl, and 5-butoxy-cyclooctyl.

The term "halo" as used herein refers to fluoro, chloro, bromo and iodo.

The term "heterocyclyl" as used herein refers to saturated and unsaturated cyclic groups composed of carbon, hydrogen, and one oxygen heteroatom. Heterocyclyl groups as refered to herein are rings of 5 or 6 members. Examples of saturated heterocyclyl radicals are tetrahydrofuranyl and tetrahydropyranyl. Examples of unsaturated heterocyclyl groups are furanyl, dihydrofuranyl, pyranyl, and the like. Preferred heterocyclyl groups are tetrahydropyran-2-yl, and tetrahydrofuran-2-yl, especially tetrahydropyran-2-yl.

The term "optionally substituted" includes the cases where a group is substituted or unsubstituted. As used herein, "optionally substituted" heterocyclyl groups may be substituted with zero, one or two lower alkyl or alkoxy radicals, as those terms are defined herein. Thus, the term "optionally substituted heterocyclyl radical" includes, for example, 2-methyltetrahydrofuran-4-yl, 2-methoxytetrahydropyran-4-yl, 2-methylfuran-4-yl, and the like.

The term "acyl" as used herein refers to groups of the formula $R_aC(O)-$, where $R_a$ is lower alkyl as defined above.

The term "protecting group" refers to a group that is used to prevent nitrogen, hydroxy or carbonyl groups from reacting undesirably during the preparation of compounds of the invention. Examples of protecting groups include but are not limited to benzyl ethers, acetonides, and esters. Protecting groups are ideally easily applied and removed under conditions unlike the reaction conditions used in the preparations. For example, benzyl ethers are stable under the acidic and basic conditions used in preparation of compounds of formula 1, but are easily removed using catalytic hydrogenolysis (e.g., $H_2$ over Pd/C). In the preparation of compounds of formula 1, tetrahydropyran-2-yl groups are particularly useful both as groups of form R and as protecting groups where R is H. In the preparation of optically active compounds of the invention (see Example 3), ethoxymethyl and methoxyethoxymethyl groups are useful for protecting the dihydropyridine nitrogen.

The term "basic addition salts" refers to salts of the subject compounds formed with organic or inorganic bases. Inorganic bases may be, for example, chloride, bromide, iodide, carbonate, bicarbonate, sulfate, nitrate, and the like. Organic bases may be, for example, acetate, benzoate, tosylate, lactate, and the like, and include optically active bases such as cinchonine, cinchonidine, quinine, quinidine, strychnine, brucine, morphine, d-α-phenethylamine, 1-arginine, dehydrobietylamine, cinchonicine, 1-2-amino-1-propanol, d-amphetamine, glucosamine, N-alkyl-glucamine, conessine, anabasine, and the like.

The term "suitable optically active base" refers to a basic compound having a chiral center which forms an insoluble salt with either the (S) isomer or the (R) isomer of a compound of formula 18 in the solvent selected. Presently preferred optically active bases are cinchonidine, cinchonine, quinine, quinidine, and N-alkyl-glucamines, where alkyl includes C1 through C10. The presently most preferred optically active base is cinchonidine.

The term "strong base" refers to strong proton-abstracting bases such as sodium hydride, sodium amide, lithium diisopropylamide, n-butyllithium, potassium t-butoxide, and the like.

The term "suitable lower alkanol solvent" refers to alcohols having from one to six carbon atoms, for example, methanol, ethanol, propanol, isopropanol, butanol, tert-butanol, pentanol, and hexanol. Preferred suitable lower alkanol solvents will dissolve the salt formed from a suitable optically active base and either (but not both) the (S) isomer or the (R) isomer of a compound of formula 18. The best lower alkanol solvents will dissolve both isomers of said salt at a first temperature range, but will dissolve only one isomer of said salt at a second temperature range. For example, where the compound of formula 18 is (RS)-1-(2-methoxyethoxymethyl)-2,6-dimethyl-3-carbomethoxy-4-(3-nitrophenyl)-5-carboxy-1,4-dihydropyridine and the optically active base is cinchonidine, both the (R) and the (S) isomer salt will dissolve in hot EtOH, whereas at lower temperatures (e.g., room temperature) the (R)-isomer salt is insoluble and crystallizes from solution. The presently most preferred solvent is ethanol.

The term "mineral acid" refers to protic acids which has a $pK_a$ lower than 5. Examples of mineral acids include HCl, HBr, $H_2SO_4$, $HNO_3$, and the like.

The term "soft acid" refers to protic organic acids which have a $pK_a$ higher than mineral acids. Examples of soft acids include acetic acid, oxalic acid, toluic acid, and the like.

The term "suitable water non-miscible solvent" refers to solvents which do not dissolve in water to an appreciable extent, which are capable of dissolving the optically active salt of formula 18, and which do not otherwise react with the compounds used. Presently preferred suitable water non-miscible solvents are diethyl ether and ethyl acetate.

The term "suitable water-miscible solvent" refers to solvents which dissolve in water to an appreciable extent, which are capable of dissolving the optically active acid of formula 19, and which do not otherwise react with the compounds used. Examples of suitable water-miscible solvents include acetone, tetrahydrofuran, DMF, $CH_3CN$, and lower alkanols such as methanol, ethanol, propanol, isopropanol, and the like. Presently preferred suitable water-miscible solvents are acetone and tetrahydrofuran.

The term "suitable aprotic solvent" refers to commonly used solvents which are devoid of easily removable protons and are otherwise inert under the reaction conditions employed. Examples of suitable aprotic solvents include acetone, tetrahydrofuran (THF), dimethylformamide (DMF), toluene, benzene, diethylether, dichloromethane, hexane, cyclohexane, dimethylsulfoxide (DMSO), hexamethylphosphoric triamide (HMPT), and the like. Preferred solvents for preparation of compounds of formula 17 are polar aprotic solvents, including acetone, THF, DMF, DMSO, and HMPT.

The term "treatment" as used herein covers any treatment of a disease in a mammal, particularly a human, and includes:

(i) preventing the disease from occurring in a subject which may be predisposed to the disease but has not yet been diagnosed as having it;

(ii) inhibiting the disease, i.e., arresting its development; or (iii) relieving the disease, i.e., causing regression of the disease.

The nomenclature used herein is a modified form of the I.U.P.A.C. convention. Compounds of the invention are named as derivatives of 1,4-dihydropyridine. The positions in the compounds are numbered beginning with the pyridine nitrogen and proceeding clockwise in all drawings of the structure. For example, the following compound is named 2,6-dimethyl-3-carbomethoxy-4-(3-nitrophenyl)-5-(3-[4-(2-methoxyethyl)-phenoxy]propoxycarbonyl)-1,4-dihydropyridine:

ture of (R) and (S) isomers at the tetrahydropyranyl radical chiral center (*). For example, the compound depicted below is (S,RS)-2,4-dimethyl-3-carbomethoxy-4-(3-nitrophenyl)-5-[3-(4-[2-(tetrahydropyran-2-yloxy)ethyl]phenoxy)propoxycarbonyl]-1,4-dihydropyridine:

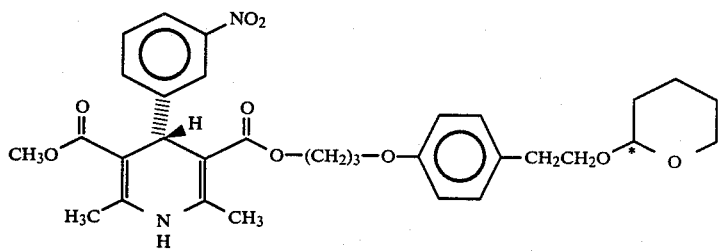

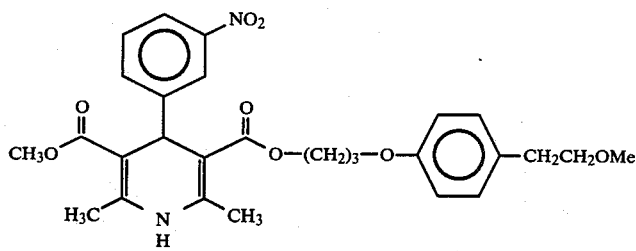

Compounds of formula I have a chiral center at C4 in the dihydropyridine ring, and thus can exist as optical isomers. Certain compounds in which R is asymmetric will thus exist as mixtures of diastereomers. In the compounds of the invention, any isomer or mixture of isomers may be used. The isomers may be separated by various methods, for example selective crystallization and column chromatography. See for example T. Shibanuma, et al., Chem. Pharm. Bull., 28, 2809–2812 (1980). Alternatively, the compounds of the invention may be prepared using optically active reactants, or by a combination of separation and chiral synthesis. The invention includes all optical isomers of any asymmetric compound of formula 1, as well as mixtures thereof. Optical isomers of compounds may be specified (+) or (−), indicating the direction the chiral center rotates a plane of polarized light. Compounds of the invention which have multiple chiral centers are prepared by condensation of one or more optically active intermediates and are specified by indicating the sign of rotation of the optically active intermediates and which dihydropyridine isomer from which the compound is prepared.

Optically active intermediates and compounds of formula 1 may also be designated using the IUPAC R–S convention, sometimes called the "sequence rule." A description of the R–S convention may be found, for example, in "Introduction to Organic Chemistry" by A. Streitwieser, Jr. and C. Heathcock, (Macmillan Pub. Co., New York, 1976), pages 110–114. Where a compound has more than one chiral center, the C4 (dihydropyridine ring) center is indicated first, with the remaining chiral centers indicated in order of increasing distance from the dihydropyridine ring. Preferred compounds of the invention have the (S) configuration at C4. An indication such as (S,RS) refers to a mixture of isomers having the (S) configuration at C4 and a mix-

ADMINISTRATION AND FORMULATION

One aspect of the present invention relates to a pharmaceutical composition useful in the treatment of cardiovascular diseases such as hypertension, congestive heart failure, angina, migraine, and vasospastic disorders, particularly in the treatment of hypertension or congestive heart disease in a mammalian subject, which composition comprises a therapeutically effective amount of a compound of formula 1, in admixture with a pharmaceutically acceptable non-toxic carrier. A therapeutically effective amount is that amount which, when administered to a mammal in need thereof, is sufficient to effect treatment, as defined above. Thus, the level of the drug in the formulation can vary from about 5 percent weight (%w) to about 95%w of the drug based on the total formulation and about 5%w to 95%w excipient. Preferably the drug is present at a level of about 10%w to about 70%w.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, aerosols, and the like. Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical, excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical carriers and their formulations are described in "Remington's Pharmaceutical Sciences" by E. W. Martin.

Another aspect of the present invention relates to a method for treating cardiovascular diseases such as hypertension, congestive heart failure, angina, migraine, and vasospastic disorders in a mammalian subject (particularly a human) which method comprises administering a therapeutically effective amount of a compound of formula 1, to a mammal in need thereof.

In the practice of the above described method of the present invention a therapeutically effective amount of the compound of formula 1 or a pharmaceutical composition containing same is administered via any of the usual and acceptable methods known in the art, either singly or in combination with another compound or compounds of the present invention or other pharmaceutical agents. These compounds or compositions can thus be administered orally, systemically (e.g., transdermally, intranasally or by suppository) or parenterally (e.g., intramuscularly, subcutaneously and intravenously), and can be administered either in the form of solid or liquid dosages including tablets, solutions, suspensions, aerosols, and the like, as discussed in more detail above. It is preferred to administer compounds of formula 1 orally.

The formulation can be administered in a single unit dosage form for continuous treatment or in a single unit dosage form ad libitum when relief of symptoms is specifically required.

The Spontaneously Hypertensive Rat (SHR) assay is an accepted test for determining antihypertensive activity. See, e.g., J. Roba, et al., *Arch. Int. Pharmacodyn.*, 200, 182 (1972). Other widely accepted tests for determining calcium entry-blocking activity include rat aortic strip assays, anesthetized dog assays, and ultrasonic two-dimensional echocardiography. See, e.g., P. Gueret, M.D., et al., *Circulation*, 62(6), 1308 (1980), and M. Tripp, *American J. of Physiology*, 232(2), H173 (1977). The compounds of the invention exhibit antihypertensive activity in the SHR assay and other assays.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount ranges from about 1.0 to about 1000 μg/kg body weight per day and preferably, for example, for antihypertensive use, from about 30 to about 500 μg/kg body weight per day. In alternative terms, for an average 70 kg adult human subject, a therapeutically effective amount in accordance herewith would be, in preferred embodiments from about 70 μg to about 70 mg per day per subject, and preferably from about 2.1 mg to 35 mg per day per subject. Generally, a therapeutically effective amount for the treatment of congestive heart disease ranges from about 1.0 to about 1000 μg/kg body weight per day, and preferably from about 30 to about 500 μg/kg body weight per day. In alternative terms, for an average 70 kg adult human subject, a therapeutically effective amount in accordance herewith would be, in preferred embodiments from about 70 μg to about 70 mg per day per subject, and preferably from about 2.1 mg to 35 mg per day per subject.

PREPARATION OF THE INVENTION

Compounds of formula 1 are prepared by the reaction sequences shown below.

SCHEME I

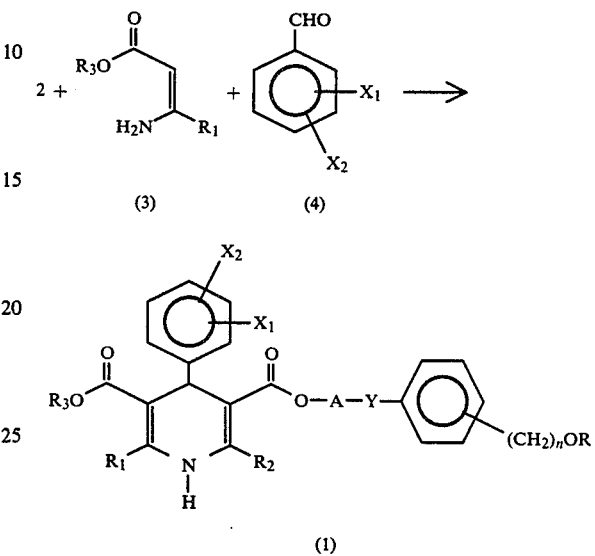

SCHEME II (Y=O)

Step 1:

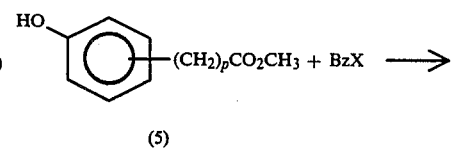

(5)

(p = n − 1)

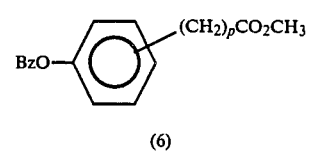

(6)

Step 2:

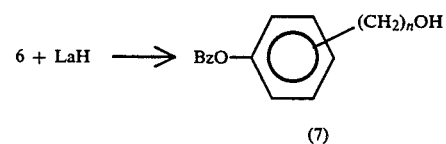

(7)

Step 3:

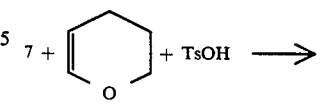

-continued
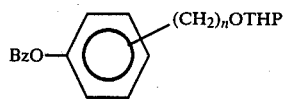
(8)
Step 4:
8 + H₂—Pd/C →
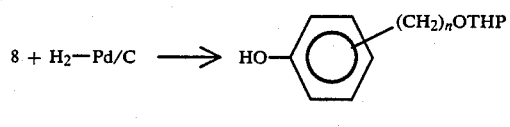
(9)
Step 5:
9 + X—A—OH →
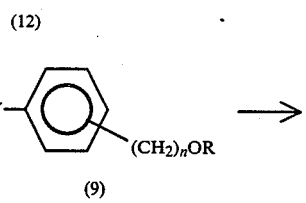
(10)
Step 6:
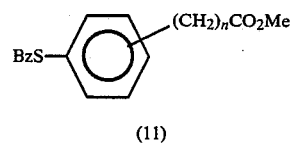
$R_2COCH_2CO_2A-O$—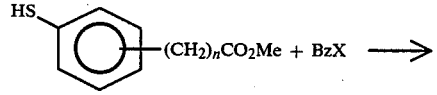
(2)
SCHEME III
(Y=S)
Step 1:
HS—⟨⟩—(CH₂)ₙCO₂Me + BzX →
BzS—⟨⟩—(CH₂)ₙCO₂Me
(11)
Step 2:
(as Scheme II, steps 2–6) →
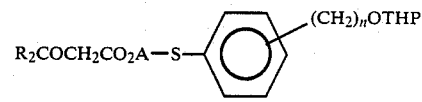
(2)
SCHEME IV
(Step 1)
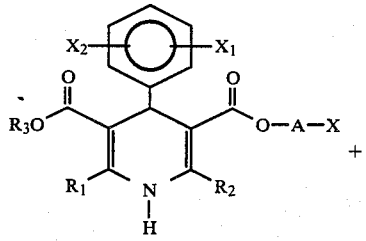
(12)
HY—⟨⟩—(CH₂)ₙOR →
(9)
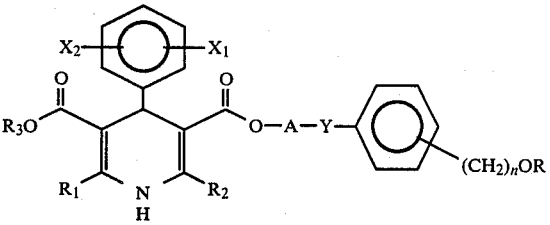
(1)
SCHEME V
Step 1:
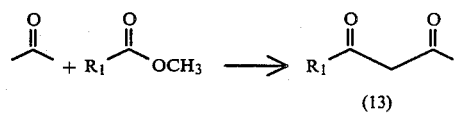
(13)
Step 2:
13 + I₂, OH⁻ → 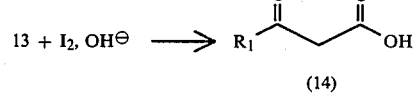
(14)
Step 3:
14 + R₃OH → 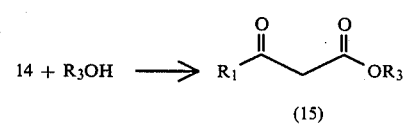
(15)
Step 4:

-continued

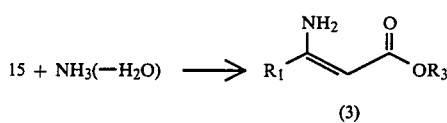

(3)

SCHEME VI

Step 1:

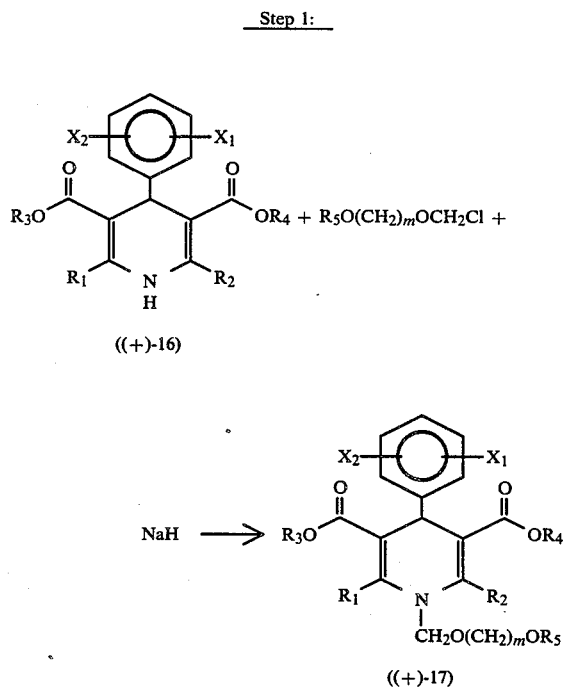

-continued

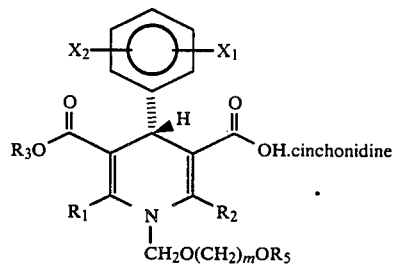

(−)-(18.cinchonidine)

Step 4:

(−)-(18.cinchonidine) + HCl ⟶ (+)-18

Step 5:

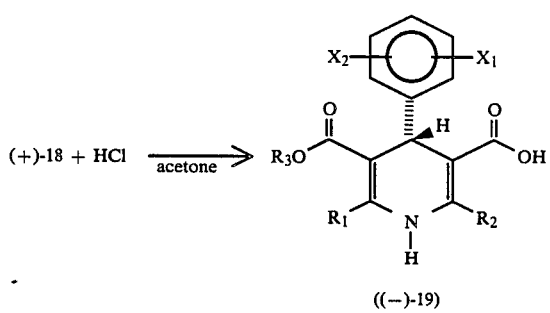

((−)-19)

In the above Schemes, n, m, R, $R_1$, $R_2$, $R_3$, $R_4$, $R_5$, $X_1$, $X_2$, A, and Y are as described above in the broadest scope of the invention. Additionally, THP is tetrahydropyran-2-yl, Ts is tosyl (p-toluenesulfonyl), X is chloro, bromo or iodo, or another leaving group such as tosyl, methanesulfonyl, or trifluoromethanesulfonyl, and Bz is benzyl. Also, $R_4$ is lower alkyl or alkoxyalkyl.

Compounds of the invention are prepared from intermediates of formulas 2, 3, and 4 according to Scheme I. Alternatively, compounds of the invention may be prepared from intermediates of formula 12 and intermediates of formula 9 according to Scheme IV. Scheme IV is particularly useful for preparing optically active compounds, as intermediates with single chiral centers (12) may be resolved prior to condensation, thus avoiding the possible difficulty associated with diastereomer resolution. Intermediates of formula 2 are prepared according to Schemes II–III. Intermediates of formula 3 may be purchased commercially, or may be made by the reaction scheme set out in Scheme V. Intermediates of formula 4 are commercially available, or may be made by methods known to those skilled in the art.

An ω-phenylalkylacetoacetate derivative (2) is reacted with an alkyl β-aminoalkenoate (3) (for example, methyl β-aminocrotonate) and a benzaldehyde derivative of formula 4 under Hantzsch dihydropyridine synthesis conditions (see, e.g., Fox, et al., *J. Org. Chem.*, 16, 1259 (1951)) to form a 4-phenyl-2,6-dialkyl-1,4-dihydropyridine dicarboxylate diester derivative (1). For example, 3-(4-[2-(tetrahydropyran-2-yloxy)ethyl]-phenoxy)propyl acetoacetate (2) is reacted with methyl β-aminocrotonate and 3-nitrobenzaldehyde to produce 2,6-dimethyl-3-carbomethoxy-4-(3-nitrophenyl)-5-(3-[4-

(2-tetrahydropyran-2-yloxyethyl)phenoxy]propoxycarbonyl)-1,4-dihydropyridine (1). (Scheme I)

Intermediates of formula 2 in which Y is O may be prepared via the reaction sequence of Scheme II.

A suitable ω-(hydroxyphenyl)alkylcarboxylic acid is selected. The carboxylic acid is esterified with a suitable alkanol, e.g., methanol, to form an alkoxycarbonylalkylphenol of formula 5. The phenol —OH group is protected by means known in the art, especially by reaction with a benzyl halide to form a benzyl ether. For example, a compound of formula 5 may be benzylated by heating at reflux with benzyl chloride under basic conditions in a suitable solvent, e.g., $K_2CO_3$ in ethanol, to form a compound of formula 6. (Scheme II, Step 1)

The compound of formula 6 is then reduced, e.g. using lithium aluminum hydride (LAH), to a hydroxyalkylbenzyloxybenzene (7). (Scheme II, Step 2)

The resulting free hydroxy group is then protected, e.g., by addition of dihydropyran to form a (2-tetrahydropyranyloxy)alkyl-(benzyloxy)benzene compound of formula 8. This reaction may be performed using dihydropyran and p-toluenesulfonic acid in a suitable solvent such as $CH_2Cl_2$. (Scheme II, Step 3) Alternatively, the compound of formula 9 may be obtained by selectively protecting a suitable 4-(hydroxyalkyl)phenol.

The group protecting the phenol OH is then removed. Benzyloxy ethers may be removed by catalytic hydrogenolysis, e.g., by using $H_2$ over a 10% Pd on carbon catalyst. The result is a tetrahydropyranyloxyalkylphenol derivative of formula 9. (Scheme II, Step 4)

Alternatively, suitable 4-(hydroxyalkyl)phenols or 4-(hydroxyalkyl)thiophenols may be protected in one step by combining a solution of the selected 4-(hydroxyalkyl)phenol or 4-(hydroxyalkyl)thiophenol in acetone with $Na_2SO_4$, dihydropyran, and a catalytic amount of oxalic acid. For example, 4-(2-hydroxyethyl)phenol in acetone is reacted with $Na_2SO_4$, distilled dihydropyran, and a catalytic amount of oxalic acid for three hours to yield 4-(2-tetrahydropyran-2-yloxyethyl)phenol (9).

The compound of formula 9 is then reacted with an ω-haloalkanol of the formula HO—A—X, e.g., 2-bromoethanol, under basic conditions in a suitable solvent (e.g., $K_2CO_3$ in ethanol) to form an alkylated derivative of formula 10. (Scheme II, Step 5) For example, 4-(2-tetrahydropyran-2-yloxyethyl)phenol may be reacted with 3-bromopropanol to form 1-[2-(tetrahydropyran-2-yloxy)ethyl]-4-(3-hydroxypropoxy)benzene (10). Compounds of the formula HO—A—X are available commercially, or may be made by methods known in the art.

A β-alkenyl-β-lactone (which can be obtained commercially or prepared by methods known in the art) is then added to the compound of formula 10 under basic conditions, e.g., using triethylamine in dimethoxyethane (DME) to form an ω-phenylalkylacetoacetate derivative (2). For example, 1-[2-(tetrahydropyran-2-yloxy)ethyl]-4-(3-hydroxypropoxy)benzene is reacted with diketene (3-buteno-β-lactone, available, e.g., from Aldrich Chemical Co.) to afford 3-(4-[2-(tetrahydropyran-2-yloxy)ethyl]phenoxy)propyl acetoacetate (2). (Scheme II, Step 6)

Intermediates of formula 2 in which Y is S may be prepared via the reaction sequence of Scheme III.

An appropriate carboxyalkylthiophenol is first esterified using methods known in the art. For example, 2-(4-thiophenyl)acetic acid is treated with methanolic HCl to yield methyl 2-(4-thiophenyl)acetate. The resulting thiol is then treated with a benzyl halide such as benzyl chloride to yield a benzylthiophenyl derivative of formula 11. For example, methyl 2-(4-thiophenyl)acetate is reacted with benzyl chloride to yield methyl 2-(4-benzylthiophenyl)acetate (11) (Scheme III, Step 1). The resulting derivative may then be treated as in steps 2 through 6 of Scheme II to produce an intermediate of formula 2 (Scheme III, Step 2). For example, methyl 2-(4-benzylthiophenyl)acetate (11) is treated as in Scheme II to produce 3-(4-[2-(tetrahydropyran-2-yloxy)ethyl]phenylthio)propyl acetoacetate (2).

Compounds of formula 1 may also be prepared via Scheme IV. A dihydropyridine of formula 12 is prepared as in Scheme I, and the compound condensed with an intermediate of formula 9 to form a compound of formula 1. For example, methyl 3-aminocrotonate, 3-nitrobenzaldehyde, and 2-cyanoethyl 3-oxobutanoate are heated together to form 2,6-dimethyl-3-carbomethoxy-4-(3-nitrophenyl)-5-(2-cyano)ethoxycarbonyl-1,4-dihydropyridine. The cyanoethyl ester is hydrolyzed using NaOH followed by HCl, converted to an acid halide (e.g., using thionyl chloride), and condensed with a compound of the formula HO—A—X, for example, 3-bromopropanol, to form a compound of formula 12. For example, 2,6-dimethyl-3-carbomethoxy-4-(3-nitrophenyl)-5-(2-cyano)ethoxycarbonyl-1,4-dihydropyridine is treated sequentially with NaOH, HCl, and thionyl chloride, then condensed with 3-bromopropanol to form 2,6-dimethyl-3-carbomethoxy-4-(3-nitrophenyl)-5-(3-bromopropoxycarbonyl)-1,4-dihydropyridine (12). The resulting bromo derivative is then condensed with 4-(2-tetrahydropyran-2-yloxyethyl)-phenol to form 2,6-dimethyl-3-carbomethoxy-4-(3-nitrophenyl)-5-(3-[4-(2-tetrahydropyran-2-yloxyethyl)-phenyl]propoxycarbonyl)-1,4-dihydropyridine (1).

Compounds of formula 1 may also be prepared by the following variation of Scheme IV, especially where optically active compounds are desired. A suitable dihydropyridine derivative acid is prepared and the optical isomers separated (where desired) following the procedure set forth by T. Shibanuma, et al., Chem. Pharm. Bull., 28, 2809–2812 (1980). For example, 2,6-dimethyl-3-carbomethoxy-4-(3-nitrophenyl)-5-carboxy-1,4-dihydropyridine is N-protected, and subsequently resolved with an optically active amine, e.g., cinchonine, to prepare (+)-2,6-dimethyl-3-carbomethoxy-4-(3-nitrophenyl)-5-carboxy-1,4-dihydropyridine (12+) and (−)-2,6-dimethyl-3-carbomethoxy-4-(3-nitrophenyl)-5-carboxy-1,4-dihydropyridine (after deprotection). The resolved dihydropyridine acid derivative is then treated with $SOCl_2$ in a suitable solvent, e.g., dichloromethane, to produce a dihydropyridine acyl chloride for condensation with an intermediate of the formula X—A—OH, where X is halo. For example, (−)-2,6-dimethyl-3-carbomethoxy-4-(3-nitrophenyl)-5-carboxy-1,4-dihydropyridine is reacted with $SOCl_2$ to yield 2,6-dimethyl-3-carbomethoxy-4-(3-nitrophenyl)-5-chlorocarbonyl-1,4-dihydropyridine, which is then reacted 3-bromopropanol to give the 3-bromopropoxy carbonyl derivative, which is then reacted with 4-(2-tetrahydropyran-2-yloxyethyl)phenol (10) in $CH_2Cl_2$ with triethylamine to generate (S,RS)-2,6-dimethyl-3-carbomethoxy-4-(3-nitrophenyl)-5-(3-[4-(2-tetrahydropyran-2-yloxyethyl)phenoxy]propoxycarbonyl)-1,4-dihydropyridine (1+).

Intermediates of formula 3 may be purchased from commercial sources, or may be prepared by methods known to those skilled in the art. For example, methyl β-aminocrotonate is available from Aldrich Chemical Co. Other β-amino-α,β-unsaturated esters may be prepared by treating the corresponding β-keto-ester with $NH_3$ with removal of water (see, e.g., A. Cope and S. Glickman, *J. Am. Chem. Soc.*, 67, 1017 (1945)). The β-keto-esters may be purchased from commercial sources, or can be prepared by means of a Claisen condensation between an alkyl alkanoate and acetone to produce a diketone, followed by oxidation and esterification as illustrated in Scheme V. Alternatively, β-keto-esters may be prepared by reacting an appropriate alcohol with 2,2,6-trimethyl-4H-1,3-dioxen-4-one (see *J. Org. Chem.*, 50, 2431–35 (1985)).

Acetone and an alkyl ketone are reacted under basic catalysis to form a diketone of formula 13. For example, the Claisen condensation of acetone and methyl butyrate yields 2,4-hexadione (Scheme V, Step 1).

The diketone is then oxidized to a β-keto acid, for example using the haloform reaction. For example, 2,4-hexadione may be treated with iodine and aqueous hydroxide to yield 3-oxopentanoic acid (14) (Scheme V, Step 2).

The β-keto acid (14) is then esterified with an alkanol of formula $R_3$-OH to yield a β-keto ester (15). For example, 3-oxopentanoic acid is heated at reflux with methanol to yield methyl 3-oxopentanoate (15) (Scheme V, Step 3).

The resulting β-keto ester is reacted with $NH_3$ under dehydrating conditions to yield a β-amino-α,β-unsaturated ester of formula 3. For example, methyl 3-oxopentanoate is heated with $NH_3$ gas and the water formed removed to yield methyl 3-aminopent-2-enoate (3) (Scheme V, Step 4).

Intermediates of formula 4 may be purchased from commercial sources, or may be prepared by methods known in the art.

The presently preferred method for preparing compounds of the invention is set forth in Scheme VI. An intermediate dihydropyridine diester derivative of formula 16 is prepared by means known in the art, e.g., by following the Hantzch method (*Ann. Chim.*, 215, 1 (1882)), using reactants selected to provide the desired $R_1$, $R_2$, $R_3$, $X_1$, and $X_2$ substitutions. The diester is then N-protected by mixing with a slight molar excess (preferably between 1.1 and 1.3 moles per mole of compound of formula 16) α-alkoxy-ω-chloromethoxyalkane and a slight molar excess (about 1.2 mol/mol 16) of a suitable strong base, preferably NaH, in a polar, aprotic solvent (preferably DMF or DMSO) at $-10°$ to $0°$ C. for between about 60 and about 100 minutes, followed by warming to about room temperature for between about 50 and 200 minutes (preferably about 60 minutes), to produce an N-protected diester of formula 17. For example, 1 mol 2,6-dimethyl-3,5-di(carbomethoxy)-4-(3-nitrophenyl)-1,4-dihydropyridine is reacted with 1.2 mol 1-methoxy-2-chloromethoxyethane and 1.2 mol NaH in DMF at $-10°$ C. for 1 hour, then allowed to warm to about 25° C. for 1 hour to produce 1-(2-methoxyethoxy)methyl-2,6-dimethyl-3,5-di(carbomethoxy)-4-(3-nitrophenyl)-1,4-dihydropyridine (17). (Scheme VI, Step 1)

The N-protected diester is then mono-saponified, e.g., by heating with an alkali metal hydroxide or alkoxide (for example, NaOH, KOH, t-BuOK) or an alkali metal carbonate (for example $K_2CO_3$) in a water miscible solvent containing 10–45% water (preferably MeOH containing 15–40% water) at reflux temperature (or between 50° C. and reflux temperature for solvents other than MeOH) for 10 to 24 hours to yield an N-protected mono-ester. For example, 1-(2-methoxyethoxy)methyl-2,6-dimethyl-3,5-di(carbomethoxy)-4-(3-nitrophenyl)-1,4-dihydropyridine in 20% $H_2O$/MeOH is heated at reflux with aqueous KOH for 16 hours to yield racemic (RS)-1-(2-methoxyethoxy)methyl-2,6-dimethyl-3-carbomethoxy-4-(3-nitrophenyl)-5-carboxy-1,4-dihydropyridine ((RS)-18). (Scheme VI, Step 2)

The racemic N-protected mono-ester of formula 18 is then dissolved in a suitable lower alkanol solvent at about the solvent reflux temperature along with a suitable optically active base, and the resulting salt allowed to crystallize as the solution cools to provide the optically resolved salt of either the (R)-18 or (S)-18. (It is preferred to recrystallize the resulting optically active salt to obtain a higher degree of purity.) For example, (RS)-1-(2-methoxyethoxy)methyl-2,6-dimethyl-3-carbomethoxy-4-(3-nitrophenyl)-5-carboxy-1,4-dihydropyridine is dissolved in EtOH at reflux temperature along with one molar equivalent of cinchonidine, and the mixture allowed to stand at room temperature overnight. The resulting crystals are recrystallized twice from EtOH to yield the pure (R)-18 salt, (R)-1-(2-methoxyethoxy)methyl-2,6-dimethyl-3-carbomethoxy-4-(3-nitrophenyl)-5-carboxy-1,4-dihydropyridine.cinchonidine. (Scheme VI, Step 3)

The resolved salt is then cleaved by acid hydrolysis using a soft acid or dilute mineral acid (preferably HCl at a concentration of about 0.6N) in a suitable water non-miscible solvent (preferably $CH_2Cl_2$ or ether) to yield the pure resolved mono-ester of formula 18. For example, (R)-1-(2-methoxyethoxy)methyl-2,6-dimethyl-3-carbomethoxy-4-(3-nitrophenyl)-5-carboxy-1,4-dihydropyridine.cinchonidine in $CH_2Cl_2$ is treated with 0.6N HCl to produce (R)-1-(2-methoxyethoxy)methyl-2,6-dimethyl-3-carbomethoxy-4-(3-nitrophenyl)-5-carboxy-1,4-dihydropyridine (18). (Scheme VI, Step 4)

The resolved mono-ester of formula 18 is then deprotected by acid hydrolysis using a dilute (about 1N to about 2N) mineral acid in a suitable water-miscible solvent (preferably acetone or THF) at a temperature between about 0° and about 15° C. for about 30 to about 120 minutes. For example, (R)-1-(2-methoxyethoxy)-methyl-2,6-dimethyl-3-carbomethoxy-4-(3-nitrophenyl)-5-carboxy-1,4-dihydropyridine is dissolved in $CH_2Cl_2$, treated with 1N HCl at 0° C., and allowed to stand for one hour at room temperature. Then, water (100 mL) is added, and the resulting precipitate is filtered to yield (R)-2,6-dimethyl-3-carbomethoxy-4-(3-nitrophenyl)-5-carboxy-1,4-dihydropyridine (19). (Scheme VI, Step 5)

Compounds of formula 1 are prepared from compounds of formula 19 following Scheme IV. For example, (R)-2,6-dimethyl-3-carbomethoxy-4-(3-nitrophenyl)-5-carboxy-1,4-dihydropyridine (19) is reacted with $SOCl_2$ to yield (S)-2,6-dimethyl-3-carbomethoxy-4-(3-nitrophenyl)-5-chlorocarbonyl-1,4-dihydropyridine, which is then reacted 3-bromopropanol to give the 3-bromopropoxy carbonyl derivative, which is then reacted with 4-(2-tetrahydropyran-2-yloxyethyl)phenol (10) in $CH_2Cl_2$ with triethylamine to generate (S,RS)-2,6-dimethyl-3-carbomethoxy-4-(3-nitrophenyl)-5-(3-[4-(2-tetrahydropyran-2-yloxyethyl)-phenoxy]propoxycarbonyl)-1,4-dihydropyridine ((S,RS)-1).

Once a compound of formula 1 has been prepared, it can be converted to other compounds of formula 1 by the appropriate reaction. For example, a compound of formula 1 in which R is tetrahydropyran-2-yl may be converted to R=H by treating the compound with TsOH in a suitable solvent, e.g., ethanol. The resulting compound is converted to compounds of the invention using known methods of etherification and esterification. For example, 2,6-dimethyl-3-carbomethoxy-4-(3-nitrophenyl)-5-(2-[4-(2-hydroxyethyl)phenoxy]ethoxycarbonyl)-1,4-dihydropyridine is treated with acetyl chloride to yield 2,6-dimethyl-3-carbomethoxy-4-(3-nitrophenyl)-5-(2-[4-(2-acetoxyethyl)phenoxy]ethoxycarbonyl)-1,4-dihydropyridine. Similarly, 2,6-dimethyl-3-carbomethoxy-4-(3-nitrophenyl)-5-(2-[4-(2-hydroxyethyl)phenoxy]ethoxycarbonyl)-1,4-dihydropyridine is treated with $K_2CO_3$ and methyl iodide to yield 2,6-dimethyl-3-carbomethoxy-4-(3-nitrophenyl)-5-(2-[4-(2-methoxyethyl)phenoxy]ethoxycarbonyl)-1,4-dihydropyridine.

In summary, compounds of formula 1 are prepared by the following methods:

An intermediate of formula 2 is reacted with a $\beta$-amino-$\alpha,\beta$-unsaturated ester of formula 3 and a benzaldehyde derivative of formula 4 under Hantzch Dihydropyridine Synthesis conditions to yield a dihydropyridine derivative of formula 1. Compounds of formula 1 in which R is tetrahydropyran-2-yl are converted to compounds in which R is H by treatment with a catalytic amount of TsOH. Such hydroxy compounds of formula 1 are then alkylated by treatment with $\omega$-haloalkanes or by treatment with an appropriate tosylheterocyclyl compound, or are acylated with standard acylating agents.

Optically active compounds of formula 1 are prepared by the following method:

A 3,5-diester-1,4-dihydropyridine derivative of formula 16 is prepared under Hantzch conditions. 1-methoxy-2-chloromethoxyethane is added in the presence of a strong base to form the N-methoxyethoxymethyl derivative. The N-alkylated derivative is then mono-saponified by heating at in an aqueous alcohol in the presence of a strong base to form an N-alkylated mono-ester. This racemic mono-ester is then optically resolved by fractional crystallization, using cinchonidine in hot ethanol to crystallize the (R) (−) isomer. The resulting resolved salt is cleaved by acid hydrolysis, followed by removal of the methoxyethoxymethyl group to produce a resolved mono-ester of formula 19. The resolved mono-ester is then treated with $SOCl_2$ in a suitable solvent, e.g., dichloromethane, to produce a dihydropyridine acyl chloride for condensation with an intermediate of the formula X—A—OH to form an optically active hydroxy-diester of formula 12. This intermediate is then reacted with a 4-($\omega$-tetrahydropyran-2-yloxyalkyl)phenol of formula 10 in $CH_2Cl_2$ with triethylamine to generate a resolved compound of formula 1. Compounds of formula 1 wherein Y is sulfinyl or sulfonyl are prepared by oxidizing compounds of formula 1 where Y is S. Compounds of formula 1 wherein R is H are prepared from compounds where R is 2-tetrahydropyranyl by hydrolysis using p-toluenesulfonic acid. Compounds of formula 1 wherein R is lower alkyl, cycloalkyl, alkoxyalkyl, cycloalkyloxyalkyl, alkoxycycloalkyl, acyl, or saturated or unsaturated 5- or 6-membered heterocyclyl optionally substituted with lower alkyl or alkoxy, wherein the heteroatom is one oxygen atom can be prepared from compounds of formula 1 where R is H by conventional methods.

The following specific description is given to enable those skilled in the art to more clearly understand and practice the invention. It should not be considered as a limitation upon the scope of the invention, but merely as being illustrative and representative thereof.

PREPARATION 1

(Preparation of 6)

(A) Methyl 4-hydroxyphenylacetate (5, 0.2 mol), obtainable from Aldrich Chemical Co. Inc., Milwaukee, Wis., is heated at reflux with benzyl chloride (25 g, 0.2 mol) and $K_2CO_3$ (25 g, 0.2 mol) in 100 mL ethanol. The product is added to dilute aqueous NaOH, extracted with ether, and purified by silica gel chromatography to yield methyl 4-benzyloxyphenylacetate (6). (Scheme II, Step 1.)

(B) Similarly, proceeding as in part A above but substituting methyl 2-hydroxyphenylacetate, methyl 3-hydroxyphenylacetate, methyl 4-hydroxyphenylpropionate, methyl 4-hydroxyphenylbutyrate, methyl 3-hydroxyphenylpropionate, 2-hydroxyphenylbutyrate, or methyl 8-(4-hydroxyphenyl)octanoate for methyl 4-hydroxyphenylacetate, the following compounds are prepared:

methyl (2-benzyloxyphenyl)acetate;
methyl (3-benzyloxyphenyl)acetate;
methyl 3-(4-benzyloxyphenyl)propionate;
methyl 4-(4-benzyloxyphenyl)butyrate;
methyl 3-(3-benzyloxyphenyl)propionate;
methyl 4-(2-benzyloxyphenyl)butyrate; and
methyl 8-(4-benzyloxyphenyl)octanoate.

PREPARATION 2

(Preparation of 7)

(A) To a suspension of lithium aluminum hydride (10.8 g, 285 mmoles) in $Et_2O$ (300 mL) was very carefully added a solution of methyl 4-(benzyloxy)phenylacetate (6, 72.8 g, 284 mmoles) in $Et_2O$ (200 mL) over 40 minutes. After an additional 30 minutes, ethyl acetate (200 mL) was added, followed by $H_2O$ (500 mL) and the mixture maintained at 0° C. The mixture was then allowed to separate into two phases. The aqueous phase was extracted with $Et_2O$ (2×500 mL). The combined extracts were dried over anhydrous $Na_2SO_4$ and evaporated to yield 1-benzyloxy-4-(2-hydroxyethyl)benzene as a white solid, (7, 64.5 g, mp=85° C.). NMR ($CDCl_3$)$\delta$ppm: 7.33(s, 4H); 6.97(q, 4H); 4.97(s, 2H); 3.67(t, 3H); 4.43(t, 3H); 4.27(s, 1H). (Scheme II, Step 2.)

(B) Similarly, proceeding as in part A above, but substituting the compounds prepared in Preparation 1(B) for methyl 4-benzyloxyphenylacetate, the following compounds are prepared:

1-benzyloxy-2-(2-hydroxyethyl)benzene;
1-benzyloxy-3-(2-hydroxyethyl)benzene;
1-benzyloxy-4-(3-hydroxypropyl)benzene;
1-benzyloxy-4-(4-hydroxybutyl)benzene;
1-benzyloxy-3-(3-hydroxypropyl)benzene;
1-benzyloxy-2-(4-hydroxybutyl)benzene; and
1-benzyloxy-4-(8-hydroxyoctyl)benzene.

PREPARATION 3

(Preparation of 8)

(A) To a solution of 1-benzyloxy-4-(2-hydroxyethyl)benzene (7, 20 g, 87.7 mmoles) in $CH_2Cl_2$ (175 mL) was added 4-toluenesulfonic acid (TsOH, 0.17 g, 0.9 mmoles) and dihydropyran (9.9 mL dropwise, 108 mmoles). The mixture was stirred for 4 h and the solvent evaporated under reduced pressure to yield 28 g of crude product. This was purified by flash chromatography (solvent=70:30 ethyl acetate:heptane). The pure fractions were pooled and the solvent evaporated to give 1-benzyloxy-4-(2-tetrahydropyran-2-yloxyethyl)-benzene (8, 26.5 g). NMR (CDCl₃)δppm: 7.30(s, 5H); 6.97(q, 4H); 4.95(s, 2H); 7.87(s, 1H); 4.2–3.4(m, 4H); 2.8(t, 2H); 1.9–1.3(m, 6H). (Scheme II, Step 3.)

(B) Similarly, proceeding as in part A above, but substituting the compounds prepared in Preparation 2(B) for 1-benzyloxy-4-(2-hydroxyethyl)benzene, the following compounds are prepared:
1-benzyloxy-2-(2-tetrahydropyran-2-yloxyethyl)benzene;
1-benzyloxy-3-(2-tetrahydropyran-2-yloxyethyl)benzene;
1-benzyloxy-4-(3-tetrahydropyran-2-yloxypropyl)benzene;
1-benzyloxy-4-(4-tetrahydrodropyran-2-yloxybutyl)benzene;
1-benzyloxy-3-(3-tetrahydropyran-2-yloxypropyl)benzene;
1-benzyloxy-2-(4-tetrahydropyran-2-yloxybutyl)benzene; and
1-benzyloxy-4-(8-tetrahydropyran-2-yloxyoctyl)benzene.

PREPARATION 4

(Preparation of 9)

(A) A solution of 1-benzyloxy-4-(2-tetrahydropyran-2-yloxyethyl)benzene (8, 27 g, 86.5 mmoles) in ethyl acetate (300 mL) was stirred with 10% Pd/C (2.7 g) under hydrogen at atmospheric pressure. After 2 hours at 55° C., the catalyst was filtered and the solvent evaporated in vacuo. The residue contained the pure debenzylated product 4-(2-tetrahydropyran-2-yloxyethyl)-phenol (9, 19 g). NMR (CDCl₃)δppm: 7.3(s, 1H); 6.88(q, 4H); 4.6(s, 1H); 4.2–3.2(m, 4H); 2.8(t, 2H); 1.63(m, 6H). (Scheme II, Step 4.)

(B) Similarly, proceeding as in part A above, but substituting the compounds prepared in Preparation 3(B) for 1-benzyloxy-4-(2-tetrahydropyran-2-yloxyethyl)benzene, the following compounds are prepared:
2-(2-tetrahydropyran-2-yloxyethyl)phenol;
3-(2-tetrahydropyran-2-yloxyethyl)phenol;
4-(3-tetrahydropyran-2-yloxypropyl)phenol;
4-(4-tetrahydropyran-2-yloxybutyl)phenol;
3-(3-tetrahydropyran-2-yloxypropyl)phenol;
2-(4-tetrahydropyran-2-yloxybutyl)phenol; and
4-(8-tetrahydropyran-2-yloxyoctyl)phenol.

(C) Compounds of formula 9 can also be prepared as follows:

Oxalic acid (64 g, 0.5 mol), Na₂SO₄ (400 g) and distilled dihydropyran (600 mL) are added to a solution of 4-(2-hydroxyethyl)phenol (600 g, 4.3 mol) in acetone (3 l) and the mixture stirred for 3 hours. The resulting solution is added to water (4 l) containing 35% NaOH solution (500 mL), and washed with CH₂Cl₂ (2X). The mixture was stirred vigorously for one hour. The organic phase was washed with water (3×1 l) and evaporated to yield 4-(2-tetrahydropyran-2-yloxyethyl)-phenol (9).

(D) Similarly, proceding as in part (C) above but substituting 4-(3-hydroxypropyl)phenol, 4-(4-hydroxybutyl)phenol, 4-(hydroxymethyl)phenol, 3-(2-hydroxyethyl)phenol, and 2-(2-hydroxyethyl)phenol for 4-(2-hydroxyethyl)phenol, the following compounds are prepared:
4-(3-tetrahydropyran-2-yloxypropyl)phenol;
4-(4-tetrahydropyran-2-yloxybutyl)phenol;
4-(tetrahydropyran-2-yloxymethyl)phenol;
3-(2-tetrahydropyran-2-yloxyethyl)phenol; and
2-(2-tetrahydropyran-2-yloxyethyl)phenol.

PREPARATION 5

(Preparation of 10)

(A) To a solution of 4-(2-tetrahydropyran-2-yloxyethyl)phenol (9, 8.0 g, 36 mmoles) in 2-butanone (100 mL) were added K₂CO₃ (10.0 g, 72 mmoles) and 3-bromopropanol (6.5 mL, 72 mmoles). The solution was refluxed 18 hours with mechanical stirring. After cooling, the mixture was filtered and the solvent removed under reduced pressure to afford 13.0 g of crude oil. This was purified by flash chromatography on silica gel (solvent=80:20 ethyl acetate:heptane). The pure fractions were pooled and the solvent removed in vacuo to give 7.0 g of 1-[2-(tetrahydropyran-2-yloxy)ethyl]-4-(3-hydroxypropy)benzene (10). NMR (CDCl₃)δppm: 7.0(q, 4H); 4.58(s, 1H)′ 4.3–3.3(m, 8H); 3.06(s, 1H); 2.83(t, 2H); 1.83(m, 2H); 1.63(m, 6H). (Scheme II, Step 5.)

(B) Similarly, proceeding as in part A above, but substituting the compounds prepared in Preparation 4(A–D) for 4-(2-tetrahydropyran-2-yloxyethyl)phenol, the following compounds are prepared:
1-[3-(tetrahydropyran-2-yloxy)propyl]-4-(3-hydroxypropoxy)benzene;
1-[4-(tetrahydropyran-2-yloxy)butyl]-4-(3-hydroxypropoxy)benzene;
1-(tetrahydropyran-2-yloxy)methyl-4-(3-hydroxypropoxy)benzene;
1-[2-(tetrahydropyran-2-yloxy)ethyl]-3-(3-hydroxypropoxy)benzene;
1-[2-(tetrahydropyran-2-yloxy)ethyl]-2-(3-hydroxypropoxy)benzene; and
1-[8-(tetrahydropyran-2-yloxy)octyl]-4-(3-hydroxypropoxy)benzene.

(C) Similarly, proceeding as in parts A and B above, but substituting 2-bromoethanol, 4-bromobutanol, 5-bromopentanol, or 8-bromooctanol for 3-bromopropanol, the following compounds are prepared:
1-[2-(tetrahydropyran-2-yloxy)ethyl]-4-(2-hydroxethoxy)benzene;
1-[2-(tetrahydropyran-2-yloxy)ethyl]-4-(4-hydroxybutoxy)benzene;
1-[3-(tetrahydropyran-2-yloxy)propyl]-4-(2-hydroxethoxy)benzene;
1-[3-(tetrahydropyran-2-yloxy)propyl]-4-(4-hydroxybutoxy)benzene;
1-[4-(tetrahydropyran-2-yloxy)butyl]-4-(2-hydroxethoxy)benzene;
1-[4-(tetrahydropyran-2-yloxy)butyl]-4-(4-hydroxybutoxy)benzene;
1-[3-(tetrahydropyran-2-yloxy)propyl]-3-(2-hydroxethoxy)benzene;
1-[4-(tetrahydropyran-2-yloxy)butyl]-2-(2-hydroxethoxy)benzene;
1-[3-(tetrahydropyran-2-yloxy)propyl]-3-(4-hydroxybutoxy)benzene;
1-[4-(tetrahydropyran-2-yloxy)butyl]-2-(4-hydroxybutoxy)benzene;
1-[8-(tetrahydropyran-2-yloxy)octyl]-4-(4-hydroxybutoxy)benzene;
1-[2-(tetrahydropyran-2-yloxy)ethyl]-4-(5-hydroxypentoxy)benzene; and
1-[2-(tetrahydropyran-2-yloxy)ethyl]-4-(8-hydroxyoctoxy)benzene.

PREPARATION 6

(Preparation of 2, Y=O)

(A) A solution of 1-[2-(tetrahydropyran-2-yloxy)ethyl]-4-(3-hydroxypropoxy)benzene (10, 24 g, 85.7 mmol) in 50 mL of dimethoxyethane and 1 mL of triethylamine was heated to reflux temperature and 8.0 mL of diketene (3-buteno-β-lactone) was added dropwise. After the addition was complete the solution was heated at reflux for 2 h. The solvents were removed in vacuo and the residue partitioned between water and ether. The ether was dried over $Na_2SO_4$ and evaporated to a residue which was purified by medium pressure chromatography on silica gel (50% ether-hexane) to afford 3-(4-[2-(tetrahydropyran-2-yloxy)ethyl]phenoxy)propyl acetoacetate (2, 25 g) as a colorless oil. (Scheme II, Step 6.)

(B) Similarly, by following the procedure of part (A) above, but substituting the compounds prepared in Preparation 5(B–C) for 1-[2-(tetrahydropyran-2-yloxy)ethyl]-4-(3-hydroxypropoxy)benzene, the following compounds are prepared:
3-(4-[3-(tetrahydropyran-2-yloxy)propyl]phenoxy)propyl acetoacetate;
3-(4-[4-(tetrahydropyran-2-yloxy)butyl]phenoxy)propyl acetoacetate;
2-(4-[2-(tetrahydropyran-2-yloxy)ethyl]phenoxy)ethyl acetoacetate;
4-(4-[2-(tetrahydropyran-2-yloxy)ethyl]phenoxy)butyl acetoacetate;
2-(4-[3-(tetrahydropyran-2-yloxy)propyl]phenoxy)ethyl acetoacetate;
4-(4-[3-(tetrahydropyran-2-yloxy)propyl]phenoxy)butyl acetoacetate;
2-(4-[4-(tetrahydropyran-2-yloxy)butyl]phenoxy) ethyl acetoacetate;
4-(4-[4-(tetrahydropyran-2-yloxy)butyl]phenoxy)butyl acetoacetate;
3-(3-[3-(tetrahydropyran-2-yloxy)propyl]phenoxy) propyl acetoacetate;
3-(3-[4-(tetrahydropyran-2-yloxy)butyl]phenoxy)propyl acetoacetate;
2-(3-[2-(tetrahydropyran-2-yloxy)ethyl]phenoxy)ethyl acetoacetate;
4-(3-[2-(tetrahydropyran-2-yloxy)ethyl]phenoxy)butyl acetoacetate;
2-(3-[3-(tetrahydropyran-2-yloxy)propyl]phenoxy)ethyl acetoacetate;
4-(3-[3-(tetrahydropyran-2-yloxy)propyl]phenoxy)butyl acetoacetate;
2-(3-[4-(tetrahydropyran-2-yloxy)butyl]phenoxy)ethyl acetoacetate;
4-(3-[4-(tetrahydropyran-2-yloxy)butyl]phenoxy)butyl acetoacetate;
3-(2-[3-(tetrahydropyran-2-yloxy)propyl]phenoxy)propyl acetoacetate;
3-(2-[4-(tetrahydropyran-2-yloxy)butyl]phenoxy)propyl acetoacetate;
2-(2-[2-(tetrahydropyran-2-yloxy)ethyl]phenoxy)ethyl acetoacetate;
4-(2-[2-tetrahydropyran-2-yloxy)ethyl]phenoxy)butyl acetoacetate;
2-(2-[3-(tetrahydropyran-2-yloxy)propyl]phenoxy)ethyl acetoacetate;
4-(2-[3-(tetrahydropyran-2-yloxy)propyl]phenoxy)butyl acetoacetate;
2-(2-[4-(tetrahydropyran-2-yloxy)butyl]phenoxy)ethyl acetoacetate;
4-(2-[4-(tetrahydropyran-2-yloxy)butyl]phenoxy)butyl acetoacetate; and
3-(4-[8-(tetrahydropyran-2-yloxy)octyl]phenoxy)propyl acetoacetate.

(C) Alternatively, 3-(4-[2-(tetrahydropyran-2-yloxy)ethyl]phenoxy)propyl acetoacetate can be prepared by heating a mixture of 1-[2-(tetrahydropyran-2-yloxy)ethyl]-4-(3-hydroxypropoxy)benzene and 2,2,6-trimethyl-4H-1,3-dioxen-4-one at 100° C., with continuing removal of the acetone produced.

By substituting 1-[2-(tetrahydropyran-2-yloxy)ethyl]-4-(2-hydroxyethoxy)benzene, 1-[2-(tetrahydropyran-2-yloxy)ethyl]-4-(4-hydroxybutoxy)benzene, 1-[3-(tetrahydropyran-2-yloxy)propyl]-4-(3-hydroxypropoxy)benzene, 1-[3-(tetrahydropyran-2-yloxy)propyl]-4-(2-hydroxyethoxy)benzene. 1-[3-(tetrahydropyran-2-yloxy)propyl]-4-(4-hydroxybutoxy)benzene, 1-[4-(tetrahydropyran-2-yloxy)butyl]-4-(3-hydroxypropoxy)benzene, 1-[4-(tetrahydropyran-2-yloxy)butyl]-4-(2-hydroxyethoxy)benzene or 1-[4-(tetrahydropyran-2-yloxy)butyl]-4-(4-hydroxybutoxy)benzene for 1-[2-(tetrahydropyran-2-yloxy)ethyl]-4-(3-hydroxypropoxy)benzene, the corresponding acetoacetate compounds can be prepared.

(D) Similarly, by following the procedure of parts (A) and (B) above, but substituting 3-penteno-β-lactone or 3-hexeno-β-lactone for diketene, the following compounds are prepared:
3-(4-[2-(tetrahydropyran-2-yloxy)ethyl]phenoxy)propyl 3-oxopentanoate;
3-(4-[3-(tetrahydropyran-2-yloxy)propyl]phenoxy)propyl 3-oxopentanoate;
3-(4-[4-(tetrahydropyran-2-yloxy)butyl]phenoxy)propyl 3-oxopentanoate;
2-(4-[2-(tetrahydropyran-2-yloxy)ethyl]phenoxy)ethyl 3-oxopentanoate;
4-(4-[2-(tetrahydropyran-2-yloxy)ethyl]phenoxy)butyl 3-oxopentanoate;
2-(4-[3-(tetrahydropyran-2-yloxy)propyl]phenoxy)ethyl 3-oxopentanoate;
4-(4-[3-(tetrahydropyran-2-yloxy)propyl]phenoxy)butyl 3-oxopentanoate;
2-(4-[4-(tetrahydropyran-2-yloxy)butyl]phenoxy)ethyl 3-oxopentanoate;
4-(4-[4-(tetrahydropyran-2-yloxy)butyl]phenoxy)butyl 3-oxopentanoate;
3-(4-[2-(tetrahydropyran-2-yloxy)ethyl]phenoxy)propyl 3-oxohexanoate;
3-(4-[3-(tetrahydropyran-2-yloxy)propyl]phenoxy)propyl 3-oxohexanoate;
3-(4-[4-(tetrahydropyran-2-yloxy)butyl]phenoxy)propyl 3-oxohexanoate;
2-(4-[2-(tetrahydropyran-2-yloxy)ethyl]phenoxy)ethyl 3-oxohexanoate;
4-(4-[2-(tetrahydropyran-2-yloxy)ethyl]phenoxy)butyl 3-oxohexanoate;
2-(4-[3-(tetrahydropyran-2-yloxy)propyl]phenoxy)ethyl 3-oxohexanoate;
4-(4-[3-(tetrahydropyran-2-yloxy)propyl]phenoxy)butyl 3-oxohexanoate;
2-(4-[4-(tetrahydropyran-2-yloxy)butyl]phenoxy)ethyl 3-oxohexanoate; and
4-(4-[4-(tetrahydropyran-2-yloxy)butyl]phenoxy)butyl 3-oxohexanoate.

PREPARATION 7

(Preparation of 11)

(A) Methyl(4-mercaptophenyl)acetate (0.2 mol) is heated at reflux with benzyl chloride (25 g, 0.2 mol) and $K_2CO_3$ (25 g, 0.2 mol) in 100 mL ethanol. The product is added to aqueous NaOH, extracted with ether, and purified by silica gel chromatography to yield methyl(4-benzylthiophenyl)acetate (3). (Scheme III, Step 1.)

(B) Similarly, proceeding as in part (A) above but substituting methyl 3-(4-mercaptophenyl)propionate, methyl 4-(4-mercaptophenyl)butyrate, methyl(2-mercaptophenyl)acetate, or methyl(3-mercaptophenyl)acetate for methyl(4-mercaptophenyl)acetate, the following compounds are prepared:

methyl 3-(4-benzylthiophenyl)propionate;
methyl 4-(4-benzylthiophenyl)butyrate;
methyl(2-benzylthiophenyl)acetate; and
methyl(3-benzylthiophenyl)acetate.

PREPARATION 8

(Preparation of 2; Y=S)

By following the directions of Preparations 1–6, but substituting the compounds prepared in Preparation 7 for the oxy-analogs, the following compounds are prepared:

2-[4-(2-tetrahydropyran-2-yloxyethyl)phenylthio]ethyl acetoacetate;
2-[4-(3-tetrahydropyran-2-yloxypropyl)phenylthio]ethyl acetoacetate;
2-[4-(4-tetrahydropyran-2-yloxybutyl)phenylthio]ethyl acetoacetate;
2-[2-(2-tetrahydropyran-2-yloxyethyl)phenylthio]ethyl acetoacetate;
2-[3-(2-tetrahydropyran-2-yloxyethyl)phenylthio]ethyl acetoacetate;
3-[4-(2-tetrahydropyran-2-yloxyethyl)phenylthio]propyl acetoacetate;
3-[4-(3-tetrahydropyran-2-yloxypropyl)phenylthio]propyl acetoacetate;
3-[4-(4-tetrahydropyran-2-yloxybutyl)phenylthio]propyl acetoacetate;
3-[2-(2-tetrahydropyran-2-yloxyethyl)phenylthio]propyl acetoacetate;
3-[3-(2-tetrahydropyran-2-yloxyethyl)phenylthio]propyl acetoacetate;
4-[4-(2-tetrahydropyran-2-yloxyethyl)phenylthio]butyl acetoacetate;
4-[4-(3-tetrahydropyran-2-yloxypropyl)phenylthio]butyl acetoacetate;
4-[4-(4-tetrahydropyran-2-yloxybutyl)phenylthio]butyl acetoacetate;
4-[2-(2-tetrahydropyran-2-yloxyethyl)phenylthio]butyl acetoacetate;
4-[3-(2-tetrahydropyran-2-yloxyethyl)phenylthio]butyl acetoacetate;
2-[4-(2-tetrahydropyran-2-yloxyethyl)phenylthio]ethyl 3-oxopentanoate;
2-[4-(3-tetrahydropyran-2-yloxypropyl)phenylthio]ethyl 3-oxopentanoate;
2-[4-(4-tetrahydropyran-2-yloxybutyl)phenylthio]ethyl 3-oxopentanoate;
2-[2-(2-tetrahydropyran-2-yloxyethyl)phenylthio]ethyl 3-oxopentanoate;
2-[3-(2-tetrahydropyran-2-yloxyethyl)phenylthio]ethyl 3-oxopentanoate;
3-[4-(2-tetrahydropyran-2-yloxyethyl)phenylthio]propyl 3-oxopentanoate;
3-[4-(3-tetrahydropyran-2-yloxypropyl)phenylthio]propyl 3-oxopentanoate;
3-[4-(4-tetrahydropyran-2-yloxybutyl)phenylthio]propyl 3-oxopentanoate;
3-[2-(2-tetrahydropyran-2-yloxyethyl)phenylthio]propyl 3-oxopentanoate;
3-[3-(2-tetrahydropyran-2-yloxyethyl)phenylthio]propyl 3-oxopentanoate;
4-[4-(2-tetrahydropyran-2-yloxyethyl)phenylthio]butyl 3-oxopentanoate;
4-[4-(3-tetrahydropyran-2-yloxypropyl)phenylthio]butyl 3-oxopentanoate;
4-[4-(4-tetrahydropyran-2-yloxybutyl)phenylthio]butyl 3-oxopentanoate;
4-[2-(2-tetrahydropyran-2-yloxyethyl)phenylthio]butyl 3-oxopentanoate;
4-[3-(2-tetrahydropyran-2-yloxyethyl)phenylthio]butyl 3-oxopentanoate;
2-[4-(2-tetrahydropyran-2-yloxyethyl)phenylthio]ethyl 3-oxohexanoate;
2-[4-(3-tetrahydropyran-2-yloxypropyl)phenylthio]ethyl 3-oxohexanoate;
2-[4-(4-tetrahydropyran-2-yloxybutyl)phenylthio]ethyl 3-oxohexanoate;
2-[2-(2-tetrahydropyran-2-yloxyethyl)phenylthio]ethyl 3-oxohexanoate;
2-[3-(2-tetrahydropyran-2-yloxyethyl)phenylthio]ethyl 3-oxohexanoate;
3-[4-(2-tetrahydropyran-2-yloxyethyl)phenylthio]propyl 3-oxohexanoate;
3-[4-(3-tetrahydropyran-2-yloxypropyl)phenylthio]propyl 3-oxohexanoate;
3-[4-(4-tetrahydropyran-2-yloxybutyl)phenylthio]propyl 3-oxohexanoate;
3-[2-(2-tetrahydropyran-2-yloxyethyl)phenylthio]propyl 3-oxohexanoate;
3-[3-(2-tetrahydropyran-2-yloxyethyl)phenylthio]propyl 3-oxohexanoate;
4-[4-(2-tetrahydropyran-2-yloxyethyl)phenylthio]butyl 3-oxohexanoate;
4-[4-(3-tetrahydropyran-2-yloxypropyl)phenylthio]butyl 3-oxohexanoate;
4-[4-(4-tetrahydropyran-2-yloxybutyl)phenylthio]butyl 3-oxohexanoate;
4-[2-(2-tetrahydropyran-2-yloxyethyl)phenylthio]butyl 3-oxohexanoate; and
4-[3-(2-tetrahydropyran-2-yloxyethyl)phenylthio]butyl 3-oxohexanoate.

PREPARATION 9

(Preparation of 12)

(A) A mixture of 3-hydroxypropionitrile (150 g, 2.11 mol) and 2,2,6-trimethyl-4H-1,3-dioxen-4-one (340 g, 2.32 mol) was heated at 110° C. until the evolution of acetone ceased. The resulting crude 2-cyanoethyl 3-oxobutanoate was used without further purification.

A mixture of 2-cyanoethy 3-oxobutanoate (83.3 g, 0.54 mol), methyl 3-aminocrotonate (61.9 g, 0.54 mol), and 3-nitrobenzaldehyde (81.3 g, 0.54 mol) in methanol (540 mL) was heated at reflux for 8 hours, then stirred overnight. The resulting precipitate was filtered, washed with methanol, and dried to produce racemic 2,6-dimethyl-3-carbomethoxy-4-(3-nitrophenyl)-5-(2-cyano)ethoxycarbonyl-1,4-dihydropyridine (mp=123° C.).

Next, a solution of NaOH (41.3 mL of 35% NaOH in 375 mL $H_2O$) was slowly added to a solution of 2,6-dimethyl-3-carbomethoxy-4-(3-nitrophenyl)-5-(2- cyano)ethoxycarbonyl-1,4-dihydropyridine (80 g, 0.21 mol) in acetone (240 mL). Then, CH$_2$Cl$_2$ (500 mL) was added and 12N HCl (41.3 mL) slowly introduced. The resulting precipitate was filtered and recrystallized from dimethylformamide/H$_2$O (175 mL DMF, 72 mL H$_2$O) to yield 2,6-dimethyl-3-carbomethoxy-4-(3-nitrophenyl)-5-carboxy-1,4-dihydropyridine (mp=242° C.).

A solution of 2,6-dimethyl-3-carbomethoxy-4-(3-nitrophenyl)-5-carboxy-1,4-dihydropyridine (107 g, 0.32 mol) in CH$_2$Cl$_2$ (520 mL) and DMF (100 mL) was cooled to 0° C. and thionyl chloride (28 mL, 0.39 mol) slowly added. The mixture was stirred at room temperature for 1 hour, then cooled to 5° C. Distilled 3-bromopropanol (35 mL, 3.9 mol) was slowly added, and the solution stirred for 1 hour at room temperature. The solution was then washed with water and the organic layer dried over sodium sulfate and evaporated under reduced pressure. The product was recrystallized from ethyl acetate to yield 2,6-dimethyl-3-carbomethoxy-4-(3-nitrophenyl)-5-(3-bromopropoxycarbonyl)-1,4-dihydropyridine (12, mp=146° C.).

(B) Similarly, proceding as in Part A above but substituting 2-bromoethanol, 4-bromobutanol, or 8-bromooctanol for 3-bromopropanol, the following compounds are prepared:
2,6-dimethyl-3-carbomethoxy-4-(3-nitrophenyl)-5-(2-bromoethoxycarbonyl)-1,4-dihydropyridine;
2,6-dimethyl-3-carbomethoxy-4-(3-nitrophenyl)-5-(4-bromobutoxycarbonyl)-1,4-dihydropyridine; and
2,6-dimethyl-3-carbomethoxy-4-(3-nitrophenyl)-5-(8-bromooctyloxycarbonyl)-1,4-dihydropyridine.

(C) Similarly, proceding as in Part (A) above, but substituting 2-nitrobenzaldehyde, 2-chlorobenzaldehyde, 3-chlorobenzaldehyde, 2,3-dichlorobenzaldehyde, 2-fluorobenzaldehyde, 3-fluorobenzaldehyde, or 2-trifluoromethylbenzaldehyde for 3-nitrobenzaldehyde, the corresponding 4-(2-nitrophenyl)-, 4-(2-chlorophenyl)-, 4-(3-chlorophenyl)-, 4-(2,3-dichlorophenyl)-, 4-(2-fluorophenyl)-, 4-(3-fluorophenyl)-, and 4-(2-trifluoromethylphenyl)-, compounds are prepared.

(D) Similarly, proceding as in Part (A) above, but substituting (+) or (−)-2,6-dimethyl-3-carbomethoxy-4-(3-nitrophenyl)-5-carboxy-1,4-dihydropyridine for racemic 2,6-dimethyl-3-carbomethoxy-4-(3-nitrophenyl)-5-carboxy-1,4-dihydropyridine, the following compounds were prepared:
(+)-2,6-dimethyl-3-carbomethoxy-4-(3-nitrophenyl)-5-(3-bromopropoxycarbonyl)-1,4-dihydropyridine (mp=115° C., $\alpha_D^{20}$=+27.8 (c=1.12 acetone)); and
(−)-2,6-dimethyl-3-carbomethoxy-4-(3-nitrophenyl)-5-(3-bromopropoxycarbonyl)-1,4-dihydropyridine (mp=113°–115° C., $\alpha_D^{20}$=−27.5 (c=1.09 acetone)).

(E) Similarly, proceding as in Parts (A) and (D) above, but substituting 3-hydroxypropionitrile, 1,3-propandiol, and 3-hydroxypropyl toluene sulfonate for 3-bromopropanol, the following compounds are prepared:
(+)-2,6-dimethyl-3-carbomethoxy-4-(3-nitrophenyl)-5-(2-cyanoethoxycarbonyl)-1,4-dihydropyridine (mp=165° C., $\alpha_D^{20}$=+30.3 (c=1.0 acetone));
(+)-2,6-dimethyl-3-carbomethoxy-4-(3-nitrophenyl)-5-(3-hydroxypropoxycarbonyl)-1,4-dihydropyridine (mp=155° C., $\alpha_D^{20}$=+18.5 (c=1.0 acetone)); and
(+)-2,6-dimethyl-3-carbomethoxy-4-(3-nitrophenyl)-5-(3-toluenesulfoxypropoxycarbonyl)-1,4-dihydropyridine (oil).

PREPARATION 10

(Preparation of 3)

(A) Intermediates of formula 3 are prepared using methods known in the art. See for example U.S. Pat. No. 3,974,275 to Bossert et al., incorporated fully herein by reference. Additionally, certain intermediates of formula 3 are commercially available, e.g., methyl β-aminocrotonate. Under Claisen reaction conditions, acetone is reacted with methyl propionate in the presence of sodium ethoxide, followed by protonation with dilute HCl, to yield 2,4-hexadione (13). The resulting diketone is then oxidized to 3-oxopentanoic acid (14) by treatment with I$_2$ or Cl$_2$ in aqueous NaOH. The resulting acid is esterified with methanol to yield methyl 3-oxopentanoate (15). The ester is then heated with ammonia, removing water during the reaction to yield methyl 3-aminopent-2-eneoate (3).

(B) Similarly, proceeding as in part (A) above but substituting methyl butyrate or methyl pentanoate for methyl propionate, the following compounds are prepared:
methyl 3-aminohex-2-eneoate; and
methyl 3-aminohept-2-eneoate.

(C) Similarly, proceeding as in parts (A–B) above but substituting ethanol, 2-propanol, or methoxyethanol for methanol, the following compounds are prepared:
ethyl 3-aminopent-2-eneoate;
ethyl 3-aminohex-2-eneoate;
ethyl 3-aminohept-2-eneoate;
isopropyl 3-aminopent-2-eneoate;
isopropyl 3-aminohex-2-eneoate;
isopropyl 3-aminohept-2-eneoate;
methoxyethyl 3-aminopent-2-eneoate;
methoxyethyl 3-aminohex-2-eneoate; and
methoxyethyl 3-aminohept-2-eneoate.

EXAMPLE 1

(Preparation of 1)

(A) A mixture of 3-(4-[2-(tetrahydropyran-2-yloxy)ethyl]phenoxy)propyl acetoacetate (2, 5 g), methyl 3-aminocrotonate (3, 2.3 g), 3-nitrobenzaldehyde (4, 2.9 g) and ethanol (70 mL) is heated at reflux for about 12 hours. The solvent is removed under reduced pressure and the residue purified using silica gel chromatography (90/10CH$_2$Cl$_2$/acetone) to yield 2,6-dimethyl-3-carbomethoxy-4-(3-nitrophenyl)-5-[3-(4-[2-(tetrahydropyran-2-yloxy)ethyl]phenoxy)propoxycarbonyl]-1,4-dihydropyridine (1, mp<55° C.).

(B) Similarly, proceding as in Part (A) above, but substituting the compounds prepared in Preparation 6(B) for 3-(4-[2-(tetrahydropyran-2-yloxy)ethyl]phenoxy)propyl acetoacetate, the following compounds are prepared:
2,6-dimethyl-3-carbomethoxy-4-(3-nitrophenyl)-5-[3-(4-[3-(tetrahydropyran-2-yloxy)propyl]phenoxy)propoxycarbonyl]-1,4-dihydropyridine (mp<50° C.);
2,6-dimethyl-3-carbomethoxy-4-(3-nitrophenyl)-5-[3-(4-[4-(tetrahydropyran-2-yloxy)butyl]phenoxy)propoxycarbonyl]-1,4-dihydropyridine;
2,6-dimethyl-3-carbomethoxy-4-(3-nitrophenyl)-5-[2-(4-[2-(tetrahydropyran-2-yloxy)ethyl]phenoxy)ethoxycarbonyl]-1,4-dihydropyridine (mp=50° C.);
2,6-dimethyl-3-carbomethoxy-4-(3-nitrophenyl)-5-[4-(4-[2-(tetrahydropyran-2-yloxy)ethyl]phenoxy)butoxycarbonyl]-1,4-dihydropyridine;

2,6-dimethyl-3-carbomethoxy-4-(3-nitrophenyl)-5-[2-(4-[3-(tetrahydropyran-2-yloxy)propyl]phenoxy)ethoxycarbonyl]-1,4-dihydropyridine (mp<50° C.);

2,6-dimethyl-3-carbomethoxy-4-(3-nitrophenyl)-5-[4-(4-[3-(tetrahydropyran-2-yloxy)propyl]phenoxy)butoxycarbonyl]-1,4-dihydropyridine;

2,6-dimethyl-3-carbomethoxy-4-(3-nitrophenyl)-5-[2-(4-[4-(tetrahydropyran-2-yloxy)butyl]phenoxy)ethoxycarbonyl]-1,4-dihydropyridine; and 2,6-dimethyl-3-carbomethoxy-4-(3-nitrophenyl)-5-[4-(4-[4-(tetrahydropyran-2-yloxy)butyl]phenoxy)butoxycarbonyl]-1,4-dihydropyridine.

(C) Similarly, proceding as in Parts (A-B) above, but substituting the compounds prepared in Preparation 6(C), the corresponding 6-ethyl and 6-propyl derivatives are prepared, for example:

2-methyl-3-carbomethoxy-4-(3-nitrophenyl)-5-[3-(4-[2-(tetrahydropyran-2-yloxy)ethyl]phenoxy)propoxycarbonyl]-6-ethyl-1,4-dihydropyridine;

2-methyl-3-carbomethoxy-4-(3-nitrophenyl)-5-[3-(4-[3-tetrahydropyran-2-yloxy)propyl]phenoxy)propoxycarbonyl]-6-ethyl-1,4-dihydropyridine; and 2-methyl-3-carbomethoxy-4-(3-nitrophenyl)-5-[3-(4-[4-(tetrahydropyran-2-yloxy)butyl]phenoxy)propoxycarbonyl]-6-ethyl-1,4-dihydropyridine.

(D) Similarly, proceding as in Part (A-C) above, but substituting the compounds prepared in Preparation 11(B) for methyl β-aminocrotonate, the corresponding 2-ethyl and 2-propyl derivatives are prepared, for example:

2-ethyl-3-(carbomethoxy)-4-(3-nitrophenyl)-5-[3-(4-[2-(tetrahydropyran-2-yloxy)ethyl]phenoxy)propoxycarbonyl]-6-methyl-1,4-dihydropyridine;

2-ethyl-3-(carbomethoxy)-4-(3-nitrophenyl)-5-[3-(4-[3-(tetrahydropyran-2-yloxy)propyl]phenoxy)propoxycarbonyl]-6-methyl-1,4-dihydropyridine;

2,6-diethyl-3-(carbomethoxy)-4-(3-nitrophenyl)-5-[3-(4-[2-(tetrahydropyran-2-yloxy)ethyl]phenoxy)propoxycarbonyl]-1,4-dihydropyridine;

2,6-diethyl-3-(carbomethoxy)-4-(3-nitrophenyl)-5-[3-(4-[3-(tetrahydropyran-2-yloxy)propyl]phenoxy)propoxycarbonyl]-1,4-dihydropyridine;

2-ethyl-3-(carbomethoxy)-4-(3-nitrophenyl)-5-[3-(4-[2-(tetrahydropyran-2-yloxy)ethyl]phenoxy)propoxycarbonyl]-6-propyl-1,4-dihydropyridine;

2-ethyl-3-(carbomethoxy)-4-(3-nitrophenyl)-5-[3-(4-[3-(tetrahydropyran-2-yloxy)propyl]phenoxy)propoxycarbonyl]-6-propyl-1,4-dihydropyridine; and 2-ethyl-3-(carbomethoxy)-4-(3-nitrophenyl)-5-[3-(4-[4-(tetrahydropyran-2-yloxy)butyl]phenoxy)propoxycarbonyl]-6-propyl-1,4-dihydropyridine.

(E) Similarly, proceeding as in Parts (A-D) above, but substituting the compounds prepared in Preparation 11(C) for methyl β-aminocrotonate, the corresponding 3-alkoxycarbonyl and 3-alkoxyalkoxycarbonyl compounds are prepared, for example:

2,6-dimethyl-3-carboethoxy-4-(3-nitrophenyl)-5-[3-(4-[3-(tetrahydropyran-2-yloxy)propyl]phenoxy)propoxycarbonyl]-1,4-dihydropyridine;

2,6-dimethyl-3-carboethoxy-4-(3-nitrophenyl)-5-[3-(4-[4-(tetrahydropyran-2-yloxy)butyl]phenoxy)propoxycarbonyl]-1,4-dihydropyridine;

2,6-dimethyl-3-(prop-yloxycarbonyl)-4-(3-nitrophenyl)-5-[2-(4-[2-(tetrahydropyran-2-yloxy)ethyl]phenoxy)ethoxycarbonyl]-1,4-dihydropyridine;

2-ethyl-3-(carbobutoxy)-4-(3-nitrophenyl)-5-[3-(4-[2-(tetrahydropyran-2-yloxy)ethyl]phenoxy)propoxycarbonyl]-6-methyl-1,4-dihydropyridine; and 2,6-dimethyl-3-(methoxyethoxycarbonyl)-4-(3-nitrophenyl)-5-[2-(4-[2-(tetrahydrofuran-2-yloxy)ethyl]phenoxy)ethoxycarbonyl]-1,4-dihydropyridine.

(F) Similarly, following the procedures of Parts (A-E) above, but substituting the compounds prepared in Preparation 8 for 3-(4-[2-(tetrahydropyran-2-yloxy)ethyl]phenoxy)propyl acetoacetate, the corresponding sulfur analogs are prepared, for example:

2,6-dimethyl-3-carbomethoxy-4-(3-nitrophenyl)-5-[3-(4-[3-(tetrahydropyran-2-yloxy)propyl]phenylthio)propoxycarbonyl]-1,4-dihydropyridine;

2,6-dimethyl-3-carbomethoxy-4-(3-nitrophenyl)-5-[3-(4-[4-(tetrahydropyran-2-yloxy)butyl]phenylthio)propoxycarbonyl]-1,4-dihydropyridine;

2,6-dimethyl-3-carbomethoxy-4-(3-nitrophenyl)-5-[2-(4-[2-(tetrahydropyran-2-yloxy)ethyl]phenylthio)ethoxycarbonyl]-1,4-dihydropyridine;

2,6-dimethyl-3-carbomethoxy-4-(3-nitrophenyl)-5-[4-(4-[2-(tetrahydropyran-2-yloxy)ethyl]phenylthio)butoxycarbonyl]-1,4-dihydropyridine;

2,6-dimethyl-3-carbomethoxy-4-(3-nitrophenyl)-5-[2-(4-[3-(tetrahydropyran-2-yloxy)propyl]phenylthio)ethoxycarbonyl]-1,4-dihydropyridine;

2,6-dimethyl-3-carbomethoxy-4-(3-nitrophenyl)-5-[4-(4-[3-(tetrahydropyran-2-yloxy)propyl]phenylthio)butoxycarbonyl]-1,4-dihydropyridine;

2,6-dimethyl-3-carbomethoxy-4-(3-nitrophenyl)-5-[2-(4-[4-(tetrahydropyran-2-yloxy)butyl]phenylthio)ethoxycarbonyl]-1,4-dihydropyridine;

2,6-dimethyl-3-carbomethoxy-4-(3-nitrophenyl)-5-[4-(4-[4-(tetrahydropyran-2-yloxy)butyl]phenylthio)butoxycarbonyl]-1,4-dihydropyridine;

2-methyl-3-carbomethoxy-4-(3-nitrophenyl)-5-[3-(4-[2-(tetrahydropyran-2-yloxy)ethyl]phenylthio)propoxycarbonyl]-6-ethyl-1,4-dihydropyridine;

2-methyl-3-carbomethoxy-4-(3-nitrophenyl)-5-[3-(4-[3-(tetrahydropyran-2-yloxy)propyl]phenylthio)propoxycarbonyl]-6-ethyl-1,4-dihydropyridine;

2-methyl-3-carbomethoxy-4-(3-nitrophenyl)-5-[3-(4-[4-(tetrahydropyran-2-yloxy)butyl]phenylthio)propoxycarbonyl]-6-ethyl-1,4-dihydropyridine;

2-ethyl-3-(carbomethoxy)-4-(3-nitrophenyl)-5-[3-(4-[2-(tetrahydropyran-2-yloxy)ethyl]phenylthio)propoxycarbonyl]-6-methyl-1,4-dihydropyridine;

2-ethyl-3-(carbomethoxy)-4-(3-nitrophenyl)-5-[3-(4-[3-(tetrahydropyran-2-yloxy)propyl]phenylthio)propoxycarbonyl]-6-methyl-1,4-dihydropyridine;

2,6-diethyl-3-(carbomethoxy)-4-(3-nitrophenyl)-5-[3-(4-[2-(tetrahydropyran-2-yloxy)ethyl]phenylthio)propoxycarbonyl]-1,4-dihydropyridine;

2,6-diethyl-3-(carbomethoxy)-4-(3-nitrophenyl)-5-[3-(4-[3-(tetrahydropyran-2-yloxy)propyl]phenylthio)propoxycarbonyl]-1,4-dihydropyridine;

2-ethyl-3-(carbomethoxy)-4-(3-nitrophenyl)-5-[3-(4-[2-(tetrahydropyran-2-yloxy)ethyl]phenylthio)propoxycarbonyl]-6-propyl-1,4-dihydropyridine;

2-ethyl-3-(carbomethoxy)-4-(3-nitrophenyl)-5-[3-(4-[3-(tetrahydropyran-2-yloxy)propyl]phenylthio)propoxycarbonyl]-6-propyl-1,4-dihydropyridine;

2-ethyl-3-(carbomethoxy)-4-(3-nitrophenyl)-5-[3-(4-[4-(tetrahydropyran-2-yloxy)butyl]phenylthio)propoxycarbonyl]-6-propyl-1,4-dihydropyridine;

2,6-dimethyl-3-carboethoxy-4-(3-nitrophenyl)-5-[3-(4-[3-(tetrahydropyran-2-yloxy)propyl]phenylthio)propoxycarbonyl]-1,4-dihydropyridine;

2,6-dimethyl-3-carboethoxy-4-(3-nitrophenyl)-5-[3-(4-[4-(tetrahydropyran-2-yloxy)butyl]phenylthio)propoxycarbonyl]-1,4-dihydropyridine;

2,6-dimethyl-3-(prop-2-yloxycarbonyl)-4-(3-nitrophenyl)-5-[2-(4-[2-(tetrahydropyran-2-yloxy)ethyl]phenylthio)ethoxycarbonyl]-1,4-dihydropyridine;

2-ethyl-3-(carbobutoxy)-4-(3-nitrophenyl)-5-[3-(4-[2-(tetrahydropyran-2-yloxy)ethyl]phenylthio)propoxycarbonyl]-6-methyl-1,4-dihydropyridine; and 2,6-dimethyl-3-(methoxyethoxycarbonyl)-4-(3-nitrophenyl)-5-[2-(4-[2-(tetrahydropyran-2-yloxy)ethyl]phenylthio)ethoxycarbonyl]-1,4-dihydropyridine.

(G) Similarly, proceding as in Parts (A–F) above, but substituting 2-nitrobenzaldehyde, 2-chlorobenzaldehyde, 3-chlorobenzaldehyde, 2,3-dichlorobenzaldehyde, 2-fluorobenzaldehyde, 3-fluorobenzaldehyde, or 2-trifluoromethylbenzaldehyde for 3-nitrobenzaldehyde, the corresponding 4-(2-nitrophenyl)-, 4-(2-chlorophenyl)-, 4-(3-chlorophenyl)-, 4-(2,3-dichlorophenyl)-, 4-(2-fluorophenyl)-, 4-(3-fluorophenyl)-, and 4-(2-trifluoromethylphenyl)- compounds are prepared, for example:

2,6-dimethyl-3-carbomethoxy-4-(2,3-dichlorophenyl)-5-[3-(4-[2-(tetrahydropyran-2-yloxy)ethyl]phenoxy)propoxycarbonyl]-1,4-dihydropyridine (mp<40° C.);

2,6-dimethyl-3-carbomethoxy-4-(2-chlorophenyl)-5-[3-(4-[2-(tetrahydropyran-2-yloxy)ethyl]phenoxy)propoxycarbonyl]-1,4-dihydropyridine;

2,6-dimethyl-3-carbomethoxy-4-(3-chlorophenyl)-5-[3-(4-[2-(tetrahydropyran-2-yloxy)ethyl]phenoxy)propoxycarbonyl]-1,4-dihydropyridine; and 2,6-dimethyl-3-carbomethoxy-4-(3-fluorophenyl)-5-[3-(4-[2-(tetrahydropyran-2-yloxy)ethyl]phenoxy)propoxycarbonyl]-1,4-dihydropyridine.

EXAMPLE 2

(Preparation of 1 by Scheme IV)

(A) 4-(2-Tetrahydropyran-2-yloxyethyl)phenol (9, 72.1 g, 0.32 mol) was added to a solution of 2,6-dimethyl-3-carbomethoxy-4-(3-nitrophenyl)-5-(3-bromopropoxycarbonyl)-1,4-dihydropyridine (12, 105 g, 0.23 mol) and $K_2CO_3$ (48 g, 0.35 mol) in acetone (700 mL), and the mixture heated at reflux overnight. After cooling, the solid was filtered, the solvent removed under reduced pressure, and the residue solubilised in $CH_2Cl_2$ (1 L). The organic layer was washed with 10% NaOH (2×100 mL) and water (2×100 mL) and dried over sodium sulfate. The solvent was evaporated under reduced pressure to provide an oil which was purified by flash chromatography (EtOAc: $CH_2Cl_2$—15:85) to yield 2,6-dimethyl-3-carbomethoxy-4-(3-nitrophenyl)-5-(3-[4-(2-tetrahydropyran-2-yloxyethyl)phenoxy]propoxycarbonyl)-1,4-dihydropyridine (1, mp<50° C.).

(B) Similarly, proceding as in Part A above but substituting the compounds prepared in Preparation 4 for 4-(2-tetrahydropyran-2-yloxyethyl)phenol, the following compounds are prepared:

2,6-dimethyl-3-carbomethoxy-4-(3-nitrophenyl)-5-(3-[4-(3-tetrahydropyran-2-yloxypropyl)phenoxy]propoxycarbonyl)-1,4-dihydropyridine; and 2,6-dimethyl-3-carbomethoxy-4-(3-nitrophenyl)-5-(3-[4-(4-tetrahydropyran-2-yloxybutyl)phenoxy]propoxycarbonyl)-1,4-dihydropyridine.

(C) Similarly, proceding as in part A above but substituting the compounds prepared in Preparation 9(D, E) for racemic 2,6-dimethyl-3-carbomethoxy-4-(3-nitrophenyl)-5-(3-bromopropoxycarbonyl)-1,4-dihydropyridine, the following compounds are prepared:

(S,RS)-2,6-dimethyl-3-carbomethoxy-4-(3-nitrophenyl)-5-(3-[4-(2-tetrahydropyran-2-yloxyethyl)-phenoxy]propoxycarbonyl)-1,4-dihydropyridine (mp=63°–67° C., $\alpha_D^{20} = +23.5$ (c=0.3 acetone)); and (R,RS)-2,6-dimethyl-3-carbomethoxy-4-(3-nitrophenyl)-5-(3-[4-(2-tetrahydropyran-2-yloxyethyl)-phenoxy]propoxycarbonyl)-1,4-dihydropyridine (mp=63°–67° C., $\alpha_D^{20} = -23.3$ (c=0.3 acetone)).

EXAMPLE 3

(Scheme IV Variation)

(A) Optically active dihydropyridine acid derivatives are prepared as described by T. Shibanuma, et al., Chem. Pharm. Bull., 28, 2809–2812 (1980). 2,6-Dimethyl-3,5-di(carbomethoxy)-4-(3-nitrophenyl)-1,4-dihydropyridine is prepared by the Hantzsch method (Ann. Chim., 215, 1 (1882)), then reacted with chloromethoxyethane and NaH to produce 1-ethoxymethyl-2,6-dimethyl-3,5-di(carbomethoxy)-4-(3-nitrophenyl)-1,4-dihydropyridine. Sodium (13.3 g) is added to 1-dimethylamino-2-propanol (150 mL) and the mixture stirred for 1 h. A solution of $H_2O$ (3.8 mL) in 1-dimethylamino-2-propanol (40 mL) is added dropwise, and the solution heated to dissolve any remaining sodium. A solution of 1-ethoxymethyl-2,6-dimethyl-3,5-di(carbomethoxy)-4-(3-nitrophenyl)-1,4-dihydropyridine (38 g) in benzene (190 mL) is then added with cooling to 0° C., and the mixture stirred for 3 h. The solvent is then removed by evaporation and the residue acidified to pH 2 by adding 3N HCl in a dry ice-acetone bath. The aqueous solution is then extracted with $CHCl_3$, and the extract washed with water, dried, and concentrated to yield racemic 1-ethoxymethyl-2,6-dimethyl-3-carbomethoxy-4-(3-nitrophenyl)-5-carboxy-1,4-dihydropyridine. The product is then dissolved in methanol (200 mL) and cinchonidine and the solvent removed. The resulting salt is then dissolved in hot ethanol (150 mL) and allowed to stand at room temperature overnight. The crystals formed are recrystallized from EtOH, treated with 0.1N HCl, and extracted with $CHCl_3$ to produce (−)-1-ethoxymethyl-2,6-dimethyl-3-carbomethoxy-4-(3-nitrophenyl)-5-carboxy-1,4-dihydropyridine (mp=134°–135°, $\alpha_D^{22} = -16.00°$). The other isomer may be recovered from the original crystallization solvent.

The resulting (−)-1-ethoxymethyl-2,6-dimethyl-3-carbomethoxy-4-(3-nitrophenyl)-5-carboxy-1,4-dihydropyridine is then dissolved in acetone (100 mL), and treated with 1N HCl (20 mL) at room temperature for 1 h. The acetone is then removed, the residue taken up in water (20 mL), and the resulting mixture extracted with EtOAc. The ethyl acetate extract is washed with water, dried, and evaporated to yield (−)-2,6-dimethyl-3-carbomethoxy-4-(3-nitrophenyl)-5-carboxy-1,4-dihydropyridine (12-(−), mp=196°–197° C., $\alpha_D^{22} = -19.6°$). The (+) isomer is similarly prepared (12-(+), mp=194°–195° C., $\alpha_D^{22} = +19.1°$).

(B) Optically active compounds of formula 1 may preferably be prepared as follows:

2,6-Dimethyl-3,5-di(carbomethoxy)-4-(3-nitrophenyl)-1,4-dihydropyridine is prepared, e.g., by the Hantzch method (Ann. Chim., 215, 1 (1882)), then reacted with 1-methoxy-2-chloromethoxyethane and NaH to produce 1-(2-methoxyethoxy)methyl-2,6-dimethyl-3,5-di(carbomethoxy)-4-(3-nitrophenyl)-1,4-dihydropyridine.

To this N-alkylated dihydropyridine derivative (71.25 g, 164 mmol) in MeOH (215 mL) and water (38 mL) is added 86% aqueous KOH (11.8 g KOH, 180 mmol). The mixture is heated at reflux for 16 hours, cooled, and water (600 mL) added. The resulting mixture is washed with ethyl acetate (2×200 mL) and concentrated in vacuo to remove MeOH. The aqueous phase is cooled to 0° C. and acidified with HCl (1.2N, 100 mL). The resulting precipitate is filtered, dried, and recrystallized from CH$_3$CN to yield racemic (RS)-1-(2-methoxyethoxy)methyl-2,6-dimethyl-3-carbomethoxy-4-(3-nitrophenyl)-5-carboxy-1,4-dihydropyridine. This product (44.5 g) is then dissolved in hot EtOH (380 mL) along with cinchonidine (31.3 g), and the mixture allowed to stand at room temperature overnight. The resulting crystals are recrystallized twice from EtOH to yield the pure (R) salt (mp=168°-170° C., $\alpha_D^{20}$=−66.2 (c=1.06 CHCl$_3$)). The crystals (28.5 g) are treated with HCl (0.6N, 500 mL) and extracted with CH$_2$Cl$_2$ (500 mL) to produce (R)-1-(2-methoxyethoxy)methyl-2,6-dimethyl-3-carbomethoxy-4-(3-nitrophenyl)-5-carboxy-1,4-dihydropyridine (mp=124° C., $\alpha_D^{20}$=+61.2° (c=1.02 CHCl$_3$)).

The resulting (R)-free base is then dissolved in acetone (100 mL), treated with HCl (1N, 120 mL) at 0° C., and allowed to stand for one hour at room temperature. Then, water (100 mL) is added, and the resulting precipitate is filtered to yield (R)-2,6-dimethyl-3-carbomethoxy-4-(3-nitrophenyl)-5-carboxy-1,4-dihydropyridine (mp=200° C., $\alpha_D^{20}$=−20.4° (c=0.51 acetone)).

(C) Similarly, proceeding as in part (B) above, one can obtain the (S)-N-alkylated salt from the first crystallization solvent by substituting cinchonine for cinchonidine (mp=180° C., $\alpha_D^{20}$=+109.4° (c=0.99 CHCl$_3$)). The salt can be cleaved as in part (B) above to yield the pure N-alkylated (S)-acid (mp=124° C., $\alpha_D^{20}$=−60.3° (c=0.98 CHCl$_3$)). The methoxyethoxymethyl group can be removed as in part (B) above to yield the pure (S) acid, (S)-2,6-dimethyl-3-carbomethoxy-4-(3-nitrophenyl)-5-carboxy-1,4-dihydropyridine (mp=200° C., $\alpha_D^{20}$=+20.3° (c=0.53 acetone)).

EXAMPLE 4

(Cleavage of Tetrahydropyran)

(A) To a solution of 2,6-dimethyl-3-carbomethoxy-4-(3-nitrophenyl)-5-(3-[4-(2-tetrahydropyran-2-yloxyethyl)phenoxy]propoxycarbonyl)-1,4-dihydropyridine (4.0 g, 6.7 mmoles) in methanol (50 mL) was added a catalytic amount of 4-toluenesulfonic acid. After 24 hours, 200 mL of CH$_2$Cl$_2$ and 100 mL of H$_2$O were added. The organic extracts were dried over anhydrous Na$_2$SO$_4$ and the solvent evaporated. The residue (3.5 g) was purified by flash chromatography (80:20 CH$_2$Cl$_2$:acetone). Evaporation of the pure fractions gave 2,6-dimethyl-3-carbomethoxy-4-(3-nitrophenyl)-5-(3-[4-(2-hydroxyethyl)phenoxy]propoxycarbonyl)-1,4-dihydropyridine (2.4 g, mp <50° C.). NMR (CDCl$_3$)δppm: 8.1–6.5(m, 9H); 5.02(s, 1H); 4.13(t, 2H); 4.0–3.4(m, 7H); 2.68(t, 2H); 2.47(s, 1H); 2.27(s, 6H); 2.3–1.8(m, 2H).

(B) Similarly, proceding as in Part A above but substituting the compounds prepared in Examples 1 or 2, the following compounds are prepared:

2,6-dimethyl-3-carbomethoxy-4-(3-nitrophenyl)-5-(3-[4-(3-hydroxypropyl)phenoxy]propoxycarbonyl)-1,4-dihydropyridine;

2,6-dimethyl-3-carbomethoxy-4-(3-nitrophenyl)-5-(3-[4-(4-hydroxybutyl)phenoxy]propoxycarbonyl)-1,4-dihydropyridine;

2,6-dimethyl-3-carbomethoxy-4-(3-nitrophenyl)-5-(2-[4-(2-hydroxyethyl)phenoxy]ethoxycarbonyl)-1,4-dihydropyridine (mp=50° C.);

2,6-dimethyl-3-carbomethoxy-4-(3-nitrophenyl)-5-(4-[4-(2-hydroxyethyl)phenoxy]butoxycarbonyl)-1,4-dihydropyridine;

2,6-dimethyl-3-carbomethoxy-4-(3-nitrophenyl)-5-(2-[4-(3-hydroxypropyl)phenoxy]ethoxycarbonyl)-1,4-dihydropyridine;

2,6-dimethyl-3-carbomethoxy-4-(3-nitrophenyl)-5-(4-[4-(3-hydroxypropyl)phenoxy]butoxycarbonyl)-1,4-dihydropyridine;

2,6-dimethyl-3-carbomethoxy-4-(3-nitrophenyl)-5-(2-[4-(4-hydroxybutyl)phenoxy]ethoxycarbonyl)-1,4-dihydropyridine;

2,6-dimethyl-3-carbomethoxy-4-(3-nitrophenyl)-5-(4-[4-(4-hydroxybutyl)phenoxy]butoxycarbonyl)-1,4-dihydropyridine;

2-methyl-3-carbomethoxy-4-(3-nitrophenyl)-5-(3-[4-(2-hydroxyethyl)phenoxy]propoxycarbonyl)-6-ethyl-1,4-dihydropyridine;

2-methyl-3-carbomethoxy-4-(3-nitrophenyl)-5-(3-[4-(3-hydroxypropyl)phenoxy]propoxycarbonyl)-6-ethyl-1,4-dihydropyridine;

2-methyl-3-carbomethoxy-4-(3-nitrophenyl)-5-(3-[4-(4-hydroxybutyl)phenoxy]propoxycarbonyl]-6-ethyl-1,4-dihydropyridine;

2-ethyl-3-(carbomethoxy)-4-(3-nitrophenyl)-5-(3-[4-(2-hydroxyethyl)phenoxy]propoxycarbonyl)-6-methyl-1,4-dihydropyridine;

2-ethyl-3-(carbomethoxy)-4-(3-nitrophenyl)-5-(3-[4-(3-hydroxypropyl)phenoxy]propoxycarbonyl)-6-methyl-1,4-dihydropyridine;

2,6-diethyl-3-(carbomethoxy)-4-(3-nitrophenyl)-5-(3-[4-(2-hydroxyethyl)phenoxy]propoxycarbonyl)-1,4-dihydropyridine;

2,6-diethyl-3-(carbomethoxy)-4-(3-nitrophenyl)-5-(3-[4-(3-hydroxypropyl)phenoxy]propoxycarbonyl)-1,4-dihydropyridine;

2-ethyl-3-(carbomethoxy)-4-(3-nitrophenyl)-5-(3-[4-(2-hydroxyethyl)phenoxy]propoxycarbonyl)-6-propyl-1,4-dihydropyridine;

2-ethyl-3-(carbomethoxy)-4-(3-nitrophenyl)-5-(3-[4-(3-hydroxypropyl)phenoxy]propoxycarbonyl)-6-propyl-1,4-dihydropyridine;

2-ethyl-3-(carbomethoxy)-4-(3-nitrophenyl)-5-(3-[4-(4-hydroxybutyl)phenoxy]propoxycarbonyl)-6-propyl-1,4-dihydropyridine;

2,6-dimethyl-3-carboethoxy-4-(3-nitrophenyl)-5-(3-[4-(3-hydroxypropyl)phenoxy]propoxycarbonyl)-1,4-dihydropyridine;

2,6-dimethyl-3-carboethoxy-4-(3-nitrophenyl)-5-(3-[4-(4-hydroxybutyl)phenoxy]propoxycarbonyl)-1,4-dihydropyridine;

2,6-dimethyl-3-(prop-2-yloxycarbonyl)-4-(3-nitrophenyl)-5-(2-[4-(2-hydroxyethyl)phenoxy]ethoxycarbonyl)-1,4-dihydropyridine;

2-ethyl-3-(carbobutoxy)-4-(3-nitrophenyl)-5-(3-[4-(2-hydroxyethyl)phenoxy]propoxycarbonyl)-6-methyl-1,4-dihydropyridine;

2,6-dimethyl-3-(methoxyethoxycarbonyl)-4-(3-nitrophenyl)-5-(2-[4-(2-hydroxyethyl)phenoxy]ethoxycarbonyl)-1,4-dihydropyridine;

2,6-dimethyl-3-carbomethoxy-4-(3-nitrophenyl)-5-(3-[4-(3-hydroxypropyl)phenylthio]propoxycarbonyl]-1,4-dihydropyridine;

2,6-dimethyl-3-carbomethoxy-4-(3-nitrophenyl)-5-(3-[4-(4-hydroxybutyl)phenylthio]propoxycarbonyl)-1,4-dihydropyridine;

2,6-dimethyl-3-carbomethoxy-4-(3-nitrophenyl)-5-(2-[4-(2-hydroxyethyl)phenylthio]ethoxycarbonyl]-1,4-dihydropyridine;

2,6-dimethyl-3-carbomethoxy-4-(3-nitrophenyl)-5-(4-[4-(2-hydroxyethyl)phenylthio]butoxycarbonyl)-1,4-dihydropyridine;

2,6-dimethyl-3-carbomethoxy-4-(3-nitrophenyl)-5-(2-[4-(3-hydroxypropyl)phenylthio]ethoxycarbonyl)-1,4-dihydropyridine;

2,6-dimethyl-3-carbomethoxy-4-(3-nitrophenyl)-5-(4-[4-(3-hydroxypropyl)phenylthio]butoxycarbonyl)-1,4-dihydropyridine;

2,6-dimethyl-3-carbomethoxy-4-(3-nitrophenyl)-5-(2-[4-(4-hydroxybutyl)phenylthio]ethoxycarbonyl)-1,4-dihydropyridine;

2,6-dimethyl-3-carbomethoxy-4-(3-nitrophenyl)-5-(4-[4-(4-hydroxybutyl)phenylthio]butoxycarbonyl)-1,4-dihydropyridine;

2-methyl-3-carbomethoxy-4-(3-nitrophenyl)-5-(3-[4-(2-hydroxyethyl)phenylthio]propoxycarbonyl)-6-ethyl-1,4-dihydropyridine;

2-methyl-3-carbomethoxy-4-(3-nitrophenyl)-5-(3-[4-(3-hydroxypropyl)phenylthio]propoxycarbonyl)-6-ethyl-1,4-dihydropyridine;

2-methyl-3-carbomethoxy-4-(3-nitrophenyl)-5-(3-[4-(4-hydroxybutyl)phenylthio]propoxycarbonyl)-6-ethyl-1,4-dihydropyridine;

2-ethyl-3-(carbomethoxy)-4-(3-nitrophenyl)-5-(3-[4-(2-hydroxyethyl)phenylthio]propoxycarbonyl)-6-methyl-1,4-dihydropyridine;

2-ethyl-3-(carbomethoxy)-4-(3-nitrophenyl)-5-(3-[4-(3-hydroxypropyl)phenylthio]propoxycarbonyl)-6-methyl-1,4-dihydropyridine;

2,6-diethyl-3-(carbomethoxy)-4-(3-nitrophenyl)-5-(3-[4-(2-hydroxyethyl)phenylthio]propoxycarbonyl)-1,4-dihydropyridine;

2,6-diethyl-3-(carbomethoxy)-4-(3-nitrophenyl)-5-(3-[4-(3-hydroxypropyl)phenylthio]propoxycarbonyl)-1,4-dihydropyridine;

2-ethyl-3-(carbomethoxy)-4-(3-nitrophenyl)-5-(3-[4-(2-hydroxyethyl)phenylthio]propoxycarbonyl)-6-propyl-1,4-dihydropyridine;

2-ethyl-3-(carbomethoxy)-4-(3-nitrophenyl)-5-(3-[4-(3-hydroxypropyl)phenylthio]propoxycarbonyl)-6-propyl-1,4-dihydropyridine;

2-ethyl-3-(carbomethoxy)-4-(3-nitrophenyl)-5-(3-[4-(4-hydroxybutyl)phenylthio]propoxycarbonyl)-6-propyl-1,4-dihydropyridine;

2,6-dimethyl-3-carboethoxy-4-(3-nitrophenyl)-5-(3-[4-(3-hydroxypropyl)phenylthio]propoxycarbonyl)-1,4-dihydropyridine;

2,6-dimethyl-3-carboethoxy-4-(3-nitrophenyl)-5-(3-[4-(4-hydroxybutyl)phenylthio]propoxycarbonyl)-1,4-dihydropyridine;

2,6-dimethyl-3-(prop-2-yloxycarbonyl)-4-(3-nitrophenyl)-5-(2-[4-(2-hydroxyethyl)phenylthio]ethoxycarbonyl)-1,4-dihydropyridine;

2-ethyl-3-(carbobutoxy)-4-(3-nitrophenyl)-5-(3-[4-(2-hydroxyethyl)phenylthio]propoxycarbonyl)-6-methyl-1,4-dihydropyridine;

2,6-dimethyl-3-(methoxyethoxycarbonyl)-4-(3-nitrophenyl)-5-(2-[4-(2-hydroxyethyl)phenylthio]ethoxycarbonyl)-1,4-dihydropyridine;

2,6-dimethyl-3-carbomethoxy-4-(2,3-dichlorophenyl)-5-(3-[4-(2-hydroxyethyl)phenoxy]propoxycarbonyl)-1,4-dihydropyridine;

2,6-dimethyl-3-carbomethoxy-4-(2-chlorophenyl)-5-(3-[4-(2-hydroxyethyl)phenoxy]propoxycarbonyl)-1,4-dihydropyridine;

2,6-dimethyl-3-carbomethoxy-4-(3-chlorophenyl)-5-(3-[4-(2-hydroxyethyl)phenoxy]propoxycarbonyl)-1,4-dihydropyridine;

2,6-dimethyl-3-carbomethoxy-4-(3-fluorophenyl)-5-(3-[4-(2-hydroxyethyl)phenoxy]propoxycarbonyl)-1,4-dihydropyridine;

2,6-dimethyl-3-carbomethoxy-4-(3-nitrophenyl)-5-(3-[4-(3-hydroxypropyl)phenoxy]propoxycarbonyl)-1,4-dihydropyridine;

2,6-dimethyl-3-carbomethoxy-4-(3-nitrophenyl)-5-(3-[4-(4-hydroxybutyl)phenoxy]propoxycarbonyl)-1,4-dihydropyridine;

(S)-2,6-dimethyl-3-carbomethoxy-4-(3-nitrophenyl)-5-(3-[4-(2-hydroxyethyl)phenoxy]propoxycarbonyl)-1,4-dihydropyridine (mp=72° C., $\alpha_D^{20} = +26.3$ (c=1.0 acetone)); and (R)-2,6-dimethyl-3-carbomethoxy-4-(3-nitrophenyl)-5-(3-[4-(2-hydroxyethyl)phenoxy]propoxycarbonyl)-1,4-dihydropyridine (mp=75° C., $\alpha_D^{20} = -27.4$ (c=1.0 acetone)).

EXAMPLE 5

(Acylation of Compounds of Formula 1)

(A) To a solution of 2,6-dimethyl-3-carbomethoxy-4-(3-nitrophenyl)-5-(2-[4-(2-hydroxyethyl)phenoxy]ethoxycarbonyl)-1,4-dihydropyridine (1.25 g, 2.52 mmoles) in $CH_2Cl_2$ (15 mL) cooled to 0° C., were added pyridine (0.25 mL, 3.10 mmoles) and acetic anhydride (0.85 mL, 9.0 mmoles). The reaction mixture was left at room temperature for 24 hours. Water (20 mL) was then added to extract the pyridine. The organic layer was dried over anhydrous $Na_2SO_4$. After evaporation of the solvent, the crude product (1.5 g) was purified by flash chromatography (solvent=93:7 $CH_2Cl_2$:acetone) to yield 2,6-dimethyl-3-methoxycarbonyl-4-(3-nitrophenyl)-5-(2-[4-(2-acetoxyethyl)phenoxy]ethoxycarbonyl)-1,4-dihydropyridine, mp=110° C. NMR ($CDCl_3$) $\delta$ppm: 8.2(m, 9H); 5.15(s, 1H); 4.5–3.9(m, 6H); 3.63(s, 3H); 2.87(t, 2H); 2.37(s, 6H); 2.07(s, 3H).

(B) Similarly, proceding as in Part A above but substituting the compounds prepared in Examples 1–3 (with the THP group removed as in Example 4) for 2,6-dimethyl-3-carbomethoxy-4-(3-nitrophenyl)-5-(2-[4-(2-hydroxyethyl)phenoxy]ethoxycarbonyl)-1,4-dihydropyridine, the corresponding acetoxy compounds are prepared, for example:

2,6-dimethyl-3-carbomethoxy-4-(3-nitrophenyl)-5-(3-[4-(2-acetoxyethyl)phenoxy]propoxycarbonyl)-1,4-dihydropyridine;

2,6-dimethyl-3-carboethoxy-4-(3-nitrophenyl)-5-(3-[4-(3-acetoxypropyl)phenoxy]propoxycarbonyl)-1,4-dihydropyridine;

2,6-dimethyl-3-carbomethoxy-4-(3-chlorophenyl)-5-(4-[4-(2-acetoxyethyl)phenoxy]butoxycarbonyl)-1,4-dihydropyridine; and 2,6-dimethyl-3-(prop-2-yloxycarbonyl)-4-(3-nitrophenyl)-5-(2-[4-(2-acetoxyethyl)phenoxy]ethoxycarbonyl)-1,4-dihydropyridine.

(C) Similarly, proceding as in Parts A and B above but substituting propanoyl chloride or butanoyl chloride (or other acylating agents) for acetic anhydride, the corresponding compounds are prepared, for example:

2,6-dimethyl-3-carbomethoxy-4-(3-nitrophenyl)-5-(3-[4-(2-propanoyloxyethyl)phenoxy]propoxycarbonyl)-1,4-dihydropyridine;

2,6-dimethyl-3-carboethoxy-4-(3-nitrophenyl)-5-(3-[4-(3-propanoyloxypropyl)phenoxy]propoxycarbonyl)-1,4-dihydropyridine;
2,6-dimethyl-3-carbomethoxy-4-(3-chlorophenyl)-5-(4-[4-(2-propanoyloxyethyl)phenoxy]butoxycarbonyl)-1,4-dihydropyridine;
2,6-dimethyl-3-(prop-2-yloxycarbonyl)-4-(3-nitrophenyl)-5-(2-[4-(2-propanoyloxyethyl)phenoxy]ethoxycarbonyl)-1,4-dihydropyridine;
2,6-dimethyl-3-carbomethoxy-4-(3-nitrophenyl)-5-(3-[4-(2-butanoyloxyethyl)phenoxy]propoxycarbonyl)-1,4-dihydropyridine;
2,6-dimethyl-3-carboethoxy-4-(3-nitrophenyl)-5-(3-[4-(3-butanoyloxypropyl)phenoxy]propoxycarbonyl)-1,4-dihydropyridine;
2,6-dimethyl-3-carbomethoxy-4-(3-chlorophenyl)-5-(4-[4-(2-butanoyloxyethyl)phenoxy]butoxycarbonyl)-1,4-dihydropyridine; and
2,6-dimethyl-3-(prop-2-yloxycarbonyl)-4-(3-nitrophenyl)-5-(2-[4-(2-butanoyloxyethyl)phenoxy]ethoxycarbonyl)-1,4-dihydropyridine.

EXAMPLE 6

(Alkylation of Compounds of Formula 1)

(A) Compounds of formula 1 in which R is H may be alkylated by treatment with a suitable haloalkane such as bromoethane, iodomethane, bromocyclohexane and the like, or a suitable haloalkoxyalkane such as chloromethoxyethane, bromomethoxycyclohexane and the like.

A solution of 2,6-dimethyl-3-carbomethoxy-4-(3-nitrophenyl)-5-(3-[4-(2-hydroxyethyl)phenoxy]propoxycarbonyl)-1,4-dihydropyridine (125 g, 0.252 moles) in acetone (700 mL) is stirred at reflux for 8 hours with $K_2CO_3$ (48 g, 0.35 mol) and n-bromopropane (61.5 g, 0.5 mol). After evaporation of the solvent, the crude product is purified by flash chromatography (solvent=93:7 $CH_2Cl_2$:acetone) to yield 2,6-dimethyl-3-methoxycarbonyl-4-(3-nitrophenyl)-5-(3-[4-(2-propoxyethyl)phenoxy]propoxycarbonyl)-1,4-dihydropyridine as an oil.

(B) Similarly, proceeding as in Part A above but substituting iodomethane, bromocyclohexane, chloromethoxypropane, or chloromethoxycyclohexane for n-bromopropane, the following compounds are prepared:
2,6-dimethyl-3-methoxycarbonyl-4-(3-nitrophenyl)-5-(3-[4-(2-methoxyethyl)phenoxy]propoxycarbonyl)-1,4-dihydropyridine (amorphous solid);
2,6-dimethyl-3-methoxycarbonyl-4-(3-nitrophenyl)-5-(3-[4-(2-cyclohexyloxyethyl)phenoxy]propoxycarbonyl)-1,4-dihydropyridine;
2,6-dimethyl-3-methoxycarbonyl-4-(3-nitrophenyl)-5-(3-[4-(2-n-propoxymethoxyethyl)phenoxy]propoxycarbonyl)-1,4-dihydropyridine (oil); and
2,6-dimethyl-3-methoxycarbonyl-4-(3-nitrophenyl)-5-(3-[4-(2-cyclohexyloxymethoxyethyl)phenoxy]propoxycarbonyl)-1,4-dihydropyridine (oil).

(C) Similarly, proceeding as in Parts A–B above but substituting (S)-2,6-dimethyl-3-carbomethoxy-4-(3-nitrophenyl)-5-(3-[4-(2-hydroxyethyl)phenoxy]propoxycarbonyl)-1,4-dihydropyridine for the racemic dihydropyridine derivative, the following compounds are prepared:
(S)-2,6-dimethyl-3-methoxycarbonyl-4-(3-nitrophenyl)-5-(3-[4-(2-methoxyethyl)phenoxy]propoxycarbonyl)-1,4-dihydropyridine;
(S)-2,6-dimethyl-3-methoxycarbonyl-4-(3-nitrophenyl)-5-(3-[4-(2-cyclohexyloxyethyl)phenoxy]propoxycarbonyl)-1,4-dihydropyridine;
(S)-2,6-dimethyl-3-methoxycarbonyl-4-(3-nitrophenyl)-5-(3-[4-(2-n-propoxymethoxyethyl)phenoxy]propoxycarbonyl)-1,4-dihydropyridine; and
(S)-2,6-dimethyl-3-methoxycarbonyl-4-(3-nitrophenyl)-5-(3-[4-(2-cyclohexyloxymethoxyethyl)phenoxy]propoxycarbonyl)-1,4-dihydropyridine (mp $\leq 50°$ C., $\alpha_D^{20}= +23.7$ (c=0.3 acetone)).

EXAMPLE 7

(Compounds of Formula 1 in Which Y is $-S(O)_{1,2}$)

(A) Compounds of formula 1 in which Y is —S(O)— may be prepared from the corresponding thio compounds.

A solution of 1.0 g of 2,6-dimethyl-3-carbomethoxy-4-(3-nitrophenyl)-5-(3-[4-(2-methoxyethyl)phenylthio]propoxycarbonyl)-1,4-dihydropyridine (1, Y=—S) and an equimolar amount of 30% hydrogen peroxide in 12 mL of acetone is allowed to stand for 12 h at 25° C. The product 2,6-dimethyl-3-carbomethoxy-4-(3-nitrophenyl)-5-(3-[4-(2-methoxyethyl)phenylsulfinyl]propoxycarbonyl)-1,4-dihydropyridine (1, Y=—S(O)—) is purified by silica gel chromatography.

(B) Similarly, proceeding as in Part A above but substituting other thio compounds of the invention, the corresponding sulfinyl compounds are produced.

(C) Compounds of formula 1 in which Y is $-S(O)_2-$ may be prepared from the corresponding sulfinyl compounds.

A solution of 1.0 g of 2,6-dimethyl-3-carbomethoxy-4-(3-nitrophenyl)-5-(3-[4-(2-methoxyethyl)phenylsulfinyl)propoxycarbonyl)-1,4-dihydropyridine (1, Y=—S(O)—) and an equimolar amount of 30% hydrogen peroxide in 12 mL of 50% acetic acid is allowed to stand for 12 h at 25° C. The product 2,6-dimethyl-3-carbomethoxy-4-(3-nitrophenyl)-5-(3-[4-(2-methoxyethyl)phenylsulfonyl]propoxycarbonyl)-1,4-dihydropyridine (1, Y=—S(O)$_2$—) is purified by silica gel chromatography.

(D) Similarly, proceeding as in Part C above but substituting other sulfinyl compounds of the invention, the corresponding sulfonyl compounds are produced.

EXAMPLE 8

(Formulations)

The following example illustrates the preparation of representative pharmaceutical formulations containing an active compound of formula 1, e.g., 2,6-dimethyl-3-carbomethoxy-4-(3-nitrophenyl)-5-(3-[4-(2-tetrahydropyran-2-yloxyethyl)phenyl]propoxycarbonyl)-1,4-dihydropyridine (1).

| I.V. Formulation | |
| --- | --- |
| Active compound | 0.01 g |
| Propylene glycol | 20.0 g |
| Polyethylene glycol 400 | 20.0 g |
| Tween 80 | 1.0 g |
| 0.9% Saline solution qs | 100.0 mL |

The active compound is dissolved in propylene glycol, polyethylene glycol 400 and Tween 80. A sufficient quantity of 0.9% saline solution is then added with stirring to provide 100 mL of the I.V. solution which is filtered through a 0.2 micron membrane filter and packaged under sterile conditions.

| TABLET FORMULATION | parts by weight |
|---|---|
| Active compound | 5.0 |
| Magnesium stearate | 0.75 |
| Starch | 0.75 |
| Lactose | 29.0 |
| PVP (polyvinylpyrrolidone) | 0.75 |

The above ingredients are combined and granulated using methanol as the solvent. The formulation is then dried and formed into tablets (containing 2 mg of active compound) with an appropriate tabletting machine.

EXAMPLE 9

(Rat Aortic Strip Assay)

Aortas are quickly removed from rats killed by a blow to the head. The tissue is cleared of connective tissue and cut into helical strips. These strips are then bathed in Krebs physiological solution at 37° C. and gassed with 95% $O_2$, 5% $CO_2$ at pH 7.4. Sustained contractions are evoked by adding either 40 mM potassium or 0.1 μM phenylephrine. Contractible tension of the muscle strips is recorded isometrically. Test compounds are added at cummulatively increasing concentrations in water or water with 2-3 drops Tween ® or 1% alcohol. The reductions in potassium and phenylephrine tensions are measured for each concentration, and a dose v. % relaxation curve is plotted for calculation of a $pIC_{50}$ value ($pIC_{50}$ is $-1$ times the log of the concentration which causes 50% inhibition of the muscle contractions). The compounds of formula 1 demonstrate activity in this assay.

EXAMPLE 10

(Spontaneously Hypertensive Rat Assay)

Twenty-four previously trained adult male spontaneously hypertensive rats are distributed into 6 groups (4 animals per group) with approximately equal mean systolic blood pressures. The 6 groups are then studied concurrently in a 2-day compound screening procedure.

Test compounds are randomly assigned to each group. Five groups receive potential antihypertensive agents and 1 control group receives vehicle only (water and Tween).

At approximately 17 hours prior to the first day of dosing food is removed from the rat cages. On the morning of Day 1, a group of 4 rats is orally dosed (by gavage) with 12.5 mg/kg or 25 mg/kg of a compound of formula 1 dissolved or suspended in water (using 2–3 drops Tween ®80) with a homogenizer at concentrations such that 0.1 mL of solution is adminstered per 10 g of body weight. At 4½ hours post dose, food is put back in the cages and the rats are allowed to eat for 2½ hours, after which food is again removed. On the morning of Day 2, rats are orally dosed as described above. Immediately after dosing, the rats are put in restrainers and placed in a heated chamber (30°±1.0° C.) for four hours. Normal feeding resumes at the end of the study on Day 2.

Systolic blood pressure (i.e., pressure at the appearance of the first pulse) is recorded using photoelectric transducers. The coccygeal arteries of 3 rats (in a horizontal group) are simultaneously occluded by pump-inflated tail cuffs that are automatically inflated to 300 mmHg and then deflated. A pressure curve and tail pulses are simultaneously monitored on an MFE recorder. Four consecutive (at 30 second intervals) traces are recorded for each rat in a given horizontal group at one, two, three and four hours post compound administration. Subsequent horizontal groups are automatically tested in the same manner.

The mean systolic blood pressure (SBP) of each rat at each observation time is calculated. The SBP of the animals in each dose group is compared to the SBP of the animals in the control group (vehicle only) at each observation time using a one-way analysis of variance test. A compound exhibiting $p \leq 0.05$ at any observation time is considered to exhibit significant antihypertensive activity. Compounds significantly decreasing blood pressure 20 mmHg or more from control values at all four observation times are considered worthy of further examination. In these instances heart rates are calculated and tested for significant change from control heart rate values using the two-tailed test. Pressures are read at hours 1, 2, 3 and 4 after dosing on both days 1 and 2. The compounds of the invention exhibited positive antihypertensive activity in this test.

EXAMPLE 11

(Anesthetized Dog Assay)

Mongrel dogs (12–15 Kg, either sex) are anesthetized with pentobarbitone sodium (35 mg/Kg initially, then 5 mg/Kg/hr i.v.) and ventilated artificially.

Recordings are made of the following cardiovascular parameters: femoral and pulmonary arterial blood pressure, cardiac left ventricular pressure, integrated heart rate (HR), left descending coronary arterial blood flow (CBF), and ascending aortic blood flow (ABF). These are displayed using a Beckman Dynograph and the analog electronic signals digitized by using a Buxco Datalogger and processed on-line using an IBMpc-XT. Use of the computer allows calculation of the mean, systolic, and diastolic aortic pressure (MAP, SAP, DAP), left ventricular stroke volume (SV), end diastolic and systolic pressure (LVEDP, LVSP), contractility (dp/dt/P), left ventricular minute work (LVMW), rate pressure product, and coronary and total peripheral vascular resistance (CVR, TPR).

Test compounds are prepared for administration in 1 mL of vehicle (5% propylene glycol, 5% glycerin, 30% EtOH, 60% $H_2O$). Appropriate controls are examined. A grooup of animals is given the test compound i.v. at 3, 10, 30, and 100 μg/Kg, and the cardiovascular parameters monitored for 15 minutes post-dose. Other groups of animals are given test compounds intraduodenally at 10 mg/Kg, and the cardiovascular parameters monitored for 2 hours post-administration.

Compounds of formula 1 demonstrate antihypertensive activity as well as other activities in this assay.

EXAMPLE 12

(Canine Echocardiography Assay)

A group of mongrel dogs, 18 to 25 kg, is chosen for the clarity of images that can be obtained from them via ultrasonic two-dimensional echocardiography (2DE). Animals from this group are used in two different models employing 2DE. In the first model the dogs are anesthetized; in the second they are conscious and non-sedated throughout the drug administration.

In both models a small branch of femoral artery is cannulated, via an arterial cutdown, with a length of water-filled tubing connected to a pressure transducer. In the conscious model, the femoral cutdown site is anesthetized with a local subcutaneous injection of 2%

Lidocaine. This transducer provides a means to monitor blood pressure. Blood pressure and ECG are recorded on a two channel chart recorder.

An ultrasound realtime scanner, connected to a 3 MgHz endfire transducer, placed in a right parasternal approach on the fourth or fifth intercostal space, produces the 2DE images. Images include a long axis view of the left ventricle defined as simultaneously imaging the apex, mitral valve, and a round left atrium. Additionally, short axis views at the high papillary muscle level are obtained. All images are recorded on video tape for later analysis. Analysis is accomplished using a computerized graphics program interfaced with the videorecorder and a bit pad.

In the first model the dogs are anesthetized with sodium pentobarbital. They are placed on their right sides on a support that allowes access, via a cutout, to the right parasternal area. Doses of 50, 100, 200, and 500 µg/kg of a compound of the invention are administered intravenously over the course of the experiment day. The compound is dissolved in 2:1 distilled water-dimethyl acetamide. Control values are obtained for each dose and further measurements are taken at 3, 5, 10, 15, and 30 minutes after administration of each dose.

In the second model the dogs are trained to stand quietly for several hours in a sling. The right parasternal area is accessed via a buttoned-down panel in the sling. Doses of 200 and 250 µg/kg of a compound of the invention are administered intravenously, dissolved in 7:1 distilled water-ethanol, as are doses of 150 and 100 µg/kg of a compound of the invention dissolved in 3:1 distilled water-dimethyl acetamide. Additionally, doses of 5, 2, 1, and 0.75 mg/kg of a compound of the invention are administered orally, with the compound in a gelatin capsule. Control values are obtained prior to each dose. During the intravenous studies additional measurements are obtained at intervals of 5, 10, 15, 30, 45, and 60 minutes after the administration of each dose. During the oral studies additional measurements are obtained at intervals of 10, 20, 30, 45, 60, 75, 90. 105, 120, and 180 minutes after the administration of each dose. Compounds of the invention demonstrate positive activity in this assay.

What is claimed is:

1. A compound of formula 1:

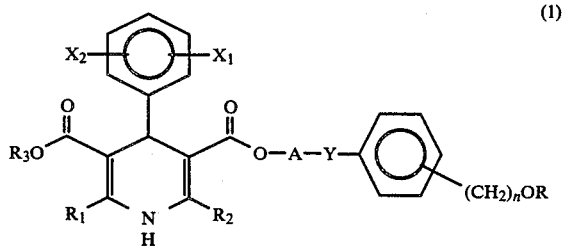

(1)

wherein
n is an integer from 1 to 4;
$R_1$ and $R_2$ are lower alkyl;
$R_3$ is a lower alkyl or alkoxyalkyl;
A is alkylene of two to eight carbon atoms;
$X_1$ and $X_2$ are each independently —$NO_2$, —$CF_3$, $CH_3O$—, —CN, —H, lower alkyl or halo;
Y is —O—, —S—, —S(O)—, or —S(O)$_2$—; and
R is H, lower alkyl, cycloalkyl, alkoxyalkyl, cycloalkyloxy-alkyl, alkoxycycloalkyl, $R_a$ C(O)—(- where $R_a$ is lower alkyl), or saturated or unsaturated 5- or 6-membered heterocyclyl optionally substituted with lower alkyl or alkoxy wherein the heteroatom is one oxygen atom.

2. The compound of claim 1 wherein $R_1$ and $R_2$ are each methyl.
3. The compound of claim 2 wherein Y is —O—.
4. The compound of claim 3 wherein the configuration at C4 of the dihydropyridine ring is (S).
5. The compound of claim 4 wherein n is 2.
6. The compound of claim 5 wherein A is propylene.
7. The compound of claim 6 wherein $X_1$ is 3-$NO_2$ and $X_2$ is —H.
8. The compound of claim 7 wherein R is tetrahydropyran-2-yl.
9. The compound of claim 7 wherein R is —H.
10. The compound of claim 7 wherein R is methyl.
11. The compound of claim 7 wherein R is propyl.
12. The compound of claim 7 wherein R is propoxymethyl.
13. The compound of claim 7 wherein R is cyclohexyloxy-methyl.
14. The compound of claim 6 wherein $X_1$ is 2-Cl and $X_2$ is 3-Cl.
15. The compound of claim 14 wherein R is tetrahydropyran-2-yl.
16. The compound of claim 14 wherein R is —H.
17. The compound of claim 5 wherein A is ethylene, $X_1$ is 3-$NO_2$ and $X_2$ is —H.
18. The compound of claim 17 wherein R is tetrahydropyran-2-yl.
19. The compound of claim 17 wherein R is —H.
20. The compound of claim 17 wherein R is methyl.
21. The compound of claim 17 wherein R is propyl.
22. The compound of claim 17 wherein R is propoxymethyl.
23. The compound of claim 17 wherein R is cyclohexyloxy-methyl.
24. The compound of claim 4 wherein n is 3.
25. The compound of claim 5 wherein A is ethylene or propylene, $X_1$ is 3-$NO_2$ and $X_2$ is —H.
26. The compound of claim 25 wherein R is tetrahydropyran-2-yl.
27. The compound of claim 25 wherein R is —H.
28. The compound of claim 25 wherein R is methyl.
29. The compound of claim 25 wherein R is propyl.
30. The compound of claim 25 wherein R is propoxymethyl.
31. The compound of claim 25 wherein R is cyclohexyloxy-methyl.
32. A pharmaceutical composition for treating a cardiovascular disease treatable with a calcium-entry antagonist, comprising a pharmaceutically acceptable excipient and an effective amount of a compound of formula 1:

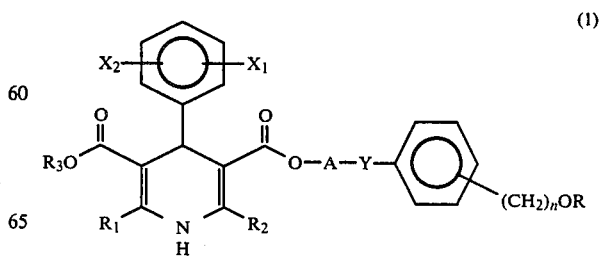

(1)

wherein n is an integer from 1 to 4;

R₁ and R₂ are lower alkyl;

R₃ is lower alkyl or alkoxyalkyl;

A is alkylene of two to eight carbon atoms;

X₁ and X₂ are each independently —NO₂, —CF₃, CH₃O—, —CN, —H, lower alkyl or halo;

Y is —O—, —S—, —S(O)—, or —S(O)₂—; and

R is H, lower alkyl, cycloalkyl, alkoxyalkyl, cycloalkyloxy-alkyl, alkoxycycloalkyl, R$_a$C(O)— (where R₁ is lower alkyl), or saturated or unsaturated 5- or 6-membered heterocyclyl optionally substituted with lower alkyl or alkoxy, wherein the heteroatom is one oxygen atom.

33. The composition of claim 32 wherein said compound of formula 1 is (S,RS)-2,6-dimethyl-3-carbomethoxy-4-(3-nitrophenyl)-5-[3-(4-[2-(tetrahydropyran-2-yloxy)ethyl]phenoxy)propoxycarbonyl]-1,4-dihydropyridine, (S)-2,6-dimethyl-3-carbomethoxy-4-(3-nitrophenyl)-5-(3-[4-(2-hydroxyethyl)phenoxy]propoxycarbonyl)-1,4-dihydropyridine, (S)-2,6-dimethyl-3-carbomethoxy-4-(3-nitrophenyl)-5-(3-[4-(2-methoxyethyl)phenoxy]propoxycarbonyl)-1,4-dihydropyridine, (S)-2,6-dimethyl-3-carbomethoxy-4-(3-nitrophenyl)-5-(3-[4-(2-propoxyethyl)phenoxy]propoxcarbonyl)-1,4-dihydropyridine, (S)-2,6-dimethyl-3-carbomethoxy-4-(3-nitrophenyl)-5-[3-(4-[2-(propoxymethoxy)ethyl]phenoxy)-propoxycarbonyl]-1,4-dihydropyridine, or (S)-2,6-dimethyl-3-carbomethoxy-4-(3-nitrophenyl)-5-[3-(4-[2-(cyclohexyloxymethoxy)ethyl]phenoxy)propoxycarbonyl]-1,4-dihydropyridine.

34. A method for treating a cardiovascular disease treatable with a calcium-entry antagonist, which method comprises administering to a subject in need thereof an effective amount of a compound of formula 1:

(1)

wherein n is an integer from 1 to 4;

R₁ and R₂ are lower alkyl;

R₃ is a lower alkyl or alkoxyalkyl;

A is alkylene of two to eight carbon atoms;

X₁ and X₂ are each independently —NO₂, —CF₃, CH₃O—, —CN, —H, lower alkyl or halo;

Y is —O—, —S—, —S(O)—, or —S(O)₂—; and

R is H, lower alkyl, cycloalkyl, alkoxyalkyl, cycloalkyloxy-alkyl, alkoxycycloalkyl, R$_a$ C(O)—(-where R$_a$ is lower alkyl), or saturated or unsaturated 5- or 6-membered heterocyclyl optionally substituted with lower alkyl or alkoxy, wherein the heteroatom is one oxygen atom.

35. The method of claim 34, wherein said compound of formula 1 is (S,RS)-2,6-dimethyl-3-carbomethoxy-4-(3-nitrophenyl)-5-[3-(4-[2-(tetrahydropyan-2-yloxy)ethyl]phenoxy)propoxycarbonyl]-1,4-dihydropyridine, (S)-2,6-dimethyl-3-carbomethoxy-4-(3-nitrophenyl)-5-(3-[4-(2-hydroxyethyl)phenoxy]propoxycarbonyl)-1,4-dihydropyridine, (S)-2,6-dimethyl-3-carbomethoxy-4-(3-nitrophenyl)-5-(3-[4-(2-methoxyethyl)phenoxy]propoxycarbonyl)-1,4-dihydropyridine, (S)-2,6-dimethyl-3-carbomethoxy-4-(3-nitrophenyl)-5-(3-[4-(2-propoxyethyl)phenoxy]propoxycarbonyl)-1,4-dihydropyridine, (S)-2,6-dimethyl-3-carbomethoxy-4-(3-nitrophenyl)-5-[3-(4-[2-(propoxymethyl)ethyl]phenoxy)-propoxycarbonyl]-1,4-dihydropyridine, or (S)-2,6-dimethyl-3-carbomethoxy-4-(3-nitrophenyl)-5-[3-(4-[2-(cyclohexyloxymethoxy)ethyl]phenoxy)propoxycarbonyl]-1,4-dihydropyridine.

* * * * *